(12) United States Patent
Appel et al.

(10) Patent No.: US 12,378,337 B2
(45) Date of Patent: Aug. 5, 2025

(54) LIPID NANODISCS SOLUBILIZED THROUGH POLY(ACRYLIC ACID-CO-STYRENE) COPOLYMERS

(71) Applicants: The Board of Trustees of the Leland Stanford Junior University, Stanford, CA (US); THE REGENTS OF THE UNIVERSITY OF CALIFORNIA, Oakland, CA (US); AARHUS UNIVERSITY, Aarhus C (DK)

(72) Inventors: Eric A. Appel, Palo Alto, CA (US); Anton Smith, San Francisco, CA (US); Henriette E. Autzen, San Francisco, CA (US); Yifan Cheng, San Francisco, CA (US)

(73) Assignees: The Board of Trustees of the Leland Stanford Junior University, Stanford, CA (US); THE REGENTS OF THE UNIVERSITY OF CALIFORNIA, Oakland, CA (US); AARHUS UNIVERSITY, Aarhus C (DK)

( * ) Notice: Subject to any disclaimer, the term of this patent is extended or adjusted under 35 U.S.C. 154(b) by 740 days.

(21) Appl. No.: 17/618,788

(22) PCT Filed: Jun. 19, 2020

(86) PCT No.: PCT/US2020/038714
§ 371 (c)(1),
(2) Date: Dec. 13, 2021

(87) PCT Pub. No.: WO2020/257637
PCT Pub. Date: Dec. 24, 2020

(65) Prior Publication Data
US 2022/0251261 A1    Aug. 11, 2022

Related U.S. Application Data

(60) Provisional application No. 62/864,696, filed on Jun. 21, 2019.

(51) Int. Cl.
*C08F 212/08* (2006.01)

(52) U.S. Cl.
CPC ........ *C08F 212/08* (2013.01); *C08F 2438/03* (2013.01)

(58) Field of Classification Search
CPC .......................... C08F 212/08; C08F 2438/03
See application file for complete search history.

(56) References Cited

U.S. PATENT DOCUMENTS

| 7,794,838 B2 | 9/2010 | Yabu et al. |
| 2016/0287741 A1 | 10/2016 | Harris et al. |

(Continued)

OTHER PUBLICATIONS

"End group removal and modification of RAFT polymers". Helen Willcock and Rachel O'Reilly. Polymer Chemistry, Issue 2, 2010. (Year: 2010).*

(Continued)

*Primary Examiner* — Ling Siu Choi
*Assistant Examiner* — Andrea Wu
(74) *Attorney, Agent, or Firm* — Pamela J. Sherwood; Bozicevic, Field & Francis LLP

(57) ABSTRACT

Provided herein are compositions including lipids and copolymers in the form of a nanodisc assembly. The subject copolymers include monomer units of styrene and monomer units selected from acrylic acid and an acrylic acid derivative. In certain cases, the copolymer is a copolymer of styrene and acrylic acid. Also provided herein, is an aqueous solution comprising the subject composition. Also provided herein, are methods for producing a nanodisc assembly, including incubation of a lipid and a subject copolymer. Further provided herein, are methods for solubilizing a membrane protein in an aqueous solution, wherein the method includes forming a nanodisc assembly of a lipid bilayer having one or more membrane proteins embedded therein, and a subject copolymer. Also provided are methods (Continued)

of solubilizing a hydrophobic constituent in an aqueous solution, including forming a nanodisc assembly of a lipid, a hydrophobic constituent, and a subject copolymer.

21 Claims, 10 Drawing Sheets

(56) References Cited

U.S. PATENT DOCUMENTS

| | | | | |
|---|---|---|---|---|
| 2018/0348577 | A1* | 12/2018 | Pousthomis | C09K 11/025 |
| 2019/0062469 | A1 | 2/2019 | Altenberg et al. | |
| 2019/0154698 | A1 | 5/2019 | Ramamoorthy et al. | |
| 2019/0346464 | A1 | 11/2019 | Ramamoorthy et al. | |

OTHER PUBLICATIONS

Mudgil et al. (2006) "Interactions of Poly(tert-butyl acrylate)-Poly(styrene) Diblock Copolymers with Lipids at the Air-Water Interface", Langmuir, 22 (18), 7672-7677.

Harding, et al. (2019) "Characterizing the structure of styrene-maleic acid copolymer-lipid nanoparticles (SMALPs) using RAFT polymerization for membrane protein spectroscopic studies." *Biophysical Journal* 116(3): 65-72.

Juarez, et al. (2019) "From polymer chemistry to structural biology: The development of SMA and related amphipathic polymers for membrane protein extraction and solubilisation." *Chemistry and physics of lipids* 221: 167-175.

Oluwole, et al. (2017) "Solubilization of membrane proteins into functional lipid-bilayer nanodiscs using a diisobutylene/maleic acid copolymer." *Angewandte Chemie International Edition* 56(7): 1919-1924.

Overduin, et al. (2019) "Advancing membrane biology with poly (styrene-co-maleic acid)-based native nanodiscs." *European Polymer Journal* 110: 63-68.

Dörr, et al. (2016) "The styrene-maleic acid copolymer: a versatile tool in membrane research." *European Biophysics Journal* 45 3-21.

Esmaili, et al. (2018) "Membrane biology visualized in nanometer-sized discs formed by styrene maleic acid polymers." *Biochimica Et Blophysica Acta (BBA)-Biomembranes* 1860(2): 257-263.

* cited by examiner

| | Initial AA | Conv. Global | Conv AA | Conv STY | AA content | AA cont. Simul. | λ | Mn kDa (calc) | Mn kDa (SEC) | Đ |
|---|---|---|---|---|---|---|---|---|---|---|
| A | 0.25 | 0.82 | 0.97 | 0.67 | 0.32 | 0.3 | -0.42 | 3.5 | 5.6 | 1.28 |
| B | 0.35 | 0.84 | 0.9 | 0.77 | 0.39 | 0.4 | -0.61 | 3.8 | 5.5 | 1.31 |
| C | 0.45 | 0.73 | 0.73 | 0.74 | 0.45 | 0.46 | -0.73 | 3.3 | 4.5 | 1.28 |
| D | 0.4 | 0.65 | 0.76 | 0.58 | 0.46 | 0.44 | -0.69 | 5.8 | 6.6 | 1.19 |
| E | 0.45 | 0.96 | 0.95 | 0.97 | 0.45 | 0.45 | -0.72 | 8.6 | 8.9 | 1.21 |
| F | 0.5 | 0.95 | 0.93 | 0.98 | 0.49 | 0.48 | -0.76 | 8.4 | 8.0 | 1.20 |
| G | 0.55 | 0.93 | 0.86 | 0.99 | 0.52 | 0.52 | -0.73 | 8.0 | 7.4 | 1.14 |
FIG. 1A
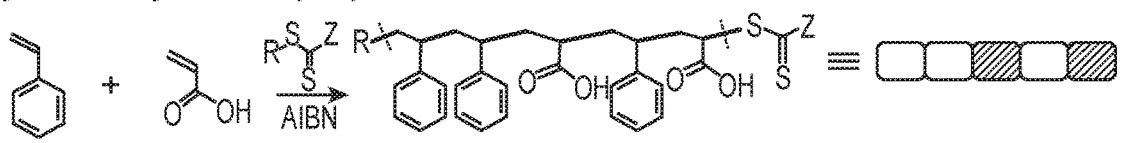
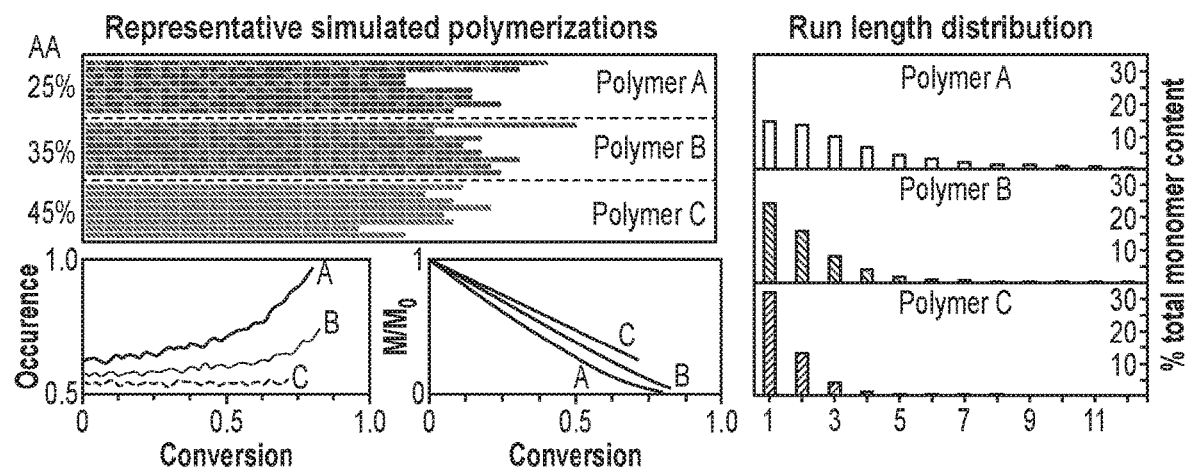
FIG. 1B

LIPID NANODISCS SOLUBILIZED THROUGH POLY(ACRYLIC ACID-CO-STYRENE) COPOLYMERS

CROSS REFERENCE

This application claims benefit of U.S. Provisional Patent Application No. 62/864,696, filed Jun. 21, 2019, which applications are incorporated herein by reference in their entirety.

INTRODUCTION

Structural biology of integral membrane proteins has been developing at a great pace since the refinement of cryo-electron microscopy. Consequently, there has been an increasing interest in reconstituting the membrane proteins in lipid-disc nanoparticles or nanodiscs to help maintain more native-like conditions. The dominating approach is currently solubilization of the membrane protein with detergents and subsequent re-lipidation of the membrane protein for insertion into a lipid-bilayer encircled by a membrane scaffold protein (MSP). This approach allows the study of the protein in a lipid environment, while the native lipids are lost. Native nanodisc forming polymers are amphipathic polymers capable of dissolving membrane proteins directly from the native lipid bilayer, circumventing the need of detergent. However, this method is still in development, with several shortcomings inherent to the system. Styrene maleic acid (SMA) copolymers, the predominant polymer for this application, are hydrolyzed copolymers of styrene and maleic anhydride. These nanodisc forming polymers are sensitive to the presence of divalent cations, have a limited pH range at which they are effective (Scheidelaar, et al. Biophys J (2016), 111, 1974-1986). Moreover, discs formed with these polymers have a low affinity to matrixes used in affinity-based purification methods, such as Ni-His tag purification or streptavidin affinity columns. In recent years research has been focused on modifying SMA with functional groups that remedy the issues inherent to SMA (Lee et al. Biochem Soc T 2016, 44, 1011-1018), however, the field has been limited in terms of controlling monomer sequence distribution (Smith et al. Biomacromolecules 2017, 18, 3706-3713; Hall et al. Biomacromoleucles 2018, 19, 761-772).

There is a need for alternative materials and techniques for the formation of improved native lipid nanodiscs for the study of membrane proteins.

SUMMARY

Provided herein are compositions including lipids and copolymers in the form of a nanodisc assembly. The subject copolymers include monomer units of styrene and monomer units selected from acrylic acid and an acrylic acid derivative. In certain cases, the copolymer is a copolymer of styrene and acrylic acid. Also provided herein, is an aqueous solution comprising the subject composition. Also provided herein, are methods for producing a nanodisc assembly, including incubation of a lipid and a subject copolymer. Further provided herein, are methods for solubilizing a membrane protein in an aqueous solution, wherein the method includes forming a nanodisc assembly of a lipid bilayer having one or more membrane proteins embedded therein, and a subject copolymer. Also provided are methods of solubilizing a hydrophobic constituent in an aqueous solution, including forming a nanodisc assembly of a lipid, a hydrophobic constituent, and a subject copolymer. In certain cases, the hydrophobic constituent is an active agent, such as a hydrophobic drug.

BRIEF DESCRIPTION OF THE FIGURES

FIG. 1A provides characterization data for exemplary copolymers.

FIG. 1B illustrates a simulation of polymer compositions of A (25% initial AA), B (35% initial AA) and C (45% initial AA), at the measured conversions. Top left shows examples of simulated chains, with each row representing one polymer. Bottom left shows probability of STY being consumed at a given conversion. Center bottom shows consumption of AA. Right shows distribution of run lengths for styrene for each polymerization.

FIG. 1D, panel B shows The AASTY polymers B and C and the conventional styrene maleic acid (SMA) polymer, SMA2000.

FIG. 2, panel B shows the area under the curves. The void and nanodisc peaks are marked with arrows.

FIG. 3, panel B illustrates SDS-PAGE of hTRPM$_4$ extracted with polymer E. FIG. 3, panels C and D illustrates cryo-EM micrograph of hTRPM$_4$ in polymer E and resulting 2D class averages, compared to MSP$_2$N$_2$ reconstituted 2D class averages.

FIG. 4, panel B shows maximum fluorescence signals from FSEC with AASTY polymers D, E, F and G and various ratios of POPC and POPG lipids with an overall increase in the content of POPG and thereby the negative charge. Values are normalized relative to the highest detected signal.

FIG. 8, panel B depicts purification of membrane proteins with nanodisc forming polymers. Cells are incubated with polymer, and the protein containing nanodiscs spontaneously form, and can be purified by affinity chromatography. SMA2000, has a statistical distribution of monomers along the chain, with multiple styrene monomers appearing in sequence, where copolymers of acrylic acid and styrene presents a more alternating sequence.

DEFINITIONS

Figure 1C:
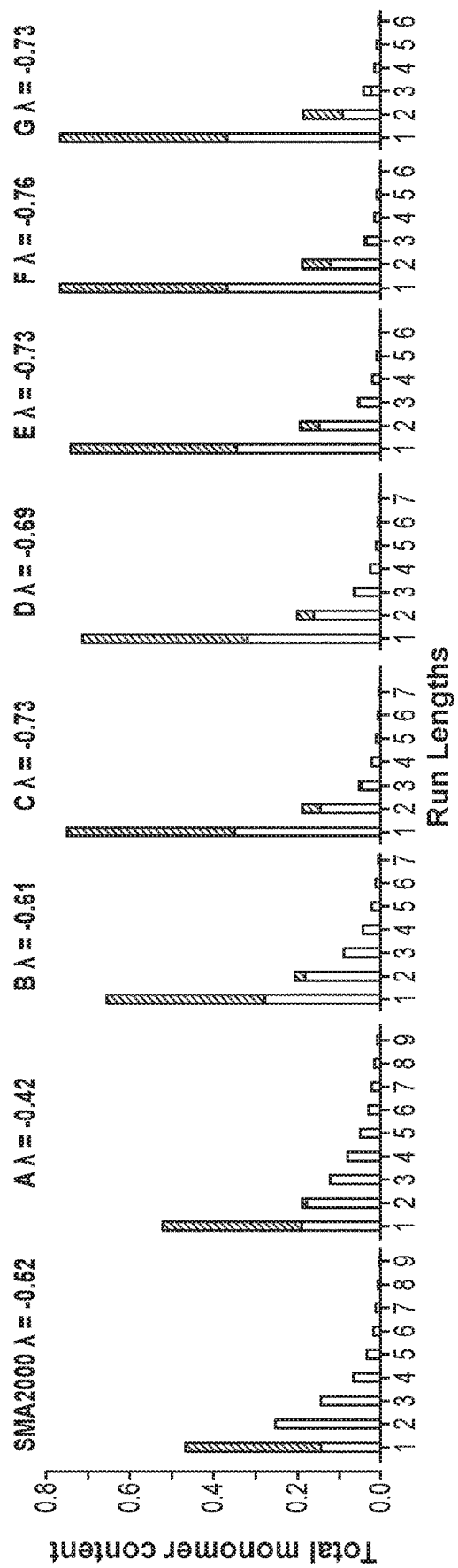
FIG. 1C illustrates the distribution of monomer run lengths, relative to total monomer content. Black denotes acrylic acid monomer (AA), grey denotes styrene monomer (STY).

As used herein, the term "salt" can mean a salt be derived from inorganic or organic bases and from inorganic or organic acids. The term "salt" encompasses pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

As used herein, the terms "determining," "measuring," "assessing," and "assaying" are used interchangeably and include both quantitative and qualitative determinations.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$—.

The term "alkyl" refers to a branched or unbranched saturated hydrocarbon group (i.e., a mono-radical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "substituted alkyl" is meant to include an alkyl group as defined herein wherein one or more carbon atoms in the alkyl chain have been optionally replaced with a heteroatom such as —O—, —N—, —S—, —S(O)n- (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO2-alkyl, —SO2-aryl, —SO2-heteroaryl, and —NRaRb, wherein R' and R" may be the same or different and are chosen from hydrogen, optionally substituted alkyl, cycloalkyl, alkenyl, cycloalkenyl, alkynyl, aryl, heteroaryl and heterocyclic.

The term "Carboxyl," "carboxy" or "carboxylate" refers to —$CO_2H$ or salts thereof.

By substituted" as in "substituted alkyl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups, and the hydrocarbyl moieties C1-C24 alkyl (including C1-C18 alkyl, further including C1-C12 alkyl, and further including C1-C6 alkyl), C2-C24 alkenyl (including C2-C18 alkenyl, further including C2-C12 alkenyl, and further including C2-C6 alkenyl), C2-C24 alkynyl (including C2-C18 alkynyl, further including C2-C12 alkynyl, and further including C2-C6 alkynyl), C5-C30 aryl (including C5-C20 aryl, and further including C5-C12 aryl), and C6-C30 aralkyl (including C6-C20 aralkyl, and further including C6-C12 aralkyl). The above-mentioned hydrocarbyl moieties may be further substituted with one or more functional groups or additional hydrocarbyl moieties such as those specifically enumerated. Unless otherwise indicated, any of the groups described herein are to be interpreted as including substituted and/or heteroatom-containing moieties, in addition to unsubstituted groups.

By the term "functional groups" is meant chemical groups such as halo, hydroxyl, sulfhydryl, C1-C24 alkoxy, C2-C24 alkenyloxy, C2-C24 alkynyloxy, C5-C20 aryloxy, acyl (including C2-C24 alkylcarbonyl (—CO-alkyl) and C6-C20 arylcarbonyl (—CO-aryl)), acyloxy (—O-acyl), C2-C24 alkoxycarbonyl (—(CO)—O-alkyl), C6-C20 aryloxycarbonyl (—(CO)—O-aryl), halocarbonyl (—CO)—X where X is halo), C2-C24 alkylcarbonato (—O—(CO)—O-alkyl), C6-C20 arylcarbonato (—O—(CO)—O-aryl), carboxy (—COOH), carboxylato (—COO—), carbamoyl (—(CO)—$NH_2$), mono-substituted C1-C24 alkylcarbamoyl (—(CO)—NH(C1-C24 alkyl)), di-substituted alkylcarbamoyl (—(CO)—N(C1-C24 alkyl)$_2$), mono-substituted arylcarbamoyl (—(CO)—NH-aryl), thiocarbamoyl (—(CS)—$NH_2$), carbamido (—NH—(CO)—$NH_2$), cyano (—C≡N), isocyano (—N+≡C—), cyanato (—O—C≡N), isocyanato (—O—N+≡C—), isothiocyanato (—S—C≡N), azido (—N=N+=N—), formyl (—(CO)—H), thioformyl (—(CS)—H), amino (—$NH_2$), mono- and di-(C1-C24 alkyl)-substituted amino, mono- and di-(C5-C20 aryl)-substituted amino, C2-C24 alkylamido (—NH—(CO)-alkyl), C5-C20 arylamido (—NH—(CO)-aryl), imino (—CR=NH where R=hydrogen, C1-C24 alkyl, C5-C20 aryl, C6-C20 alkaryl, C6-C20 aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O—), C1-C24 alkylsulfanyl (—S—alkyl; also termed "alkylthio"), arylsulfanyl (—S-aryl; also termed "arylthio"), C1-C24 alkylsulfinyl (—(SO)-alkyl), C5-C20 arylsulfinyl (—(SO)-aryl), C1-C24 alkylsulfonyl (—SO$_2$-alkyl), C5-C20 arylsulfonyl (—SO$_2$-aryl), phosphono (—P(O)(OH)$_2$), phosphonato (—P(O)(O—)$_2$), phosphinato (—P(O)(O—)), phospho (—PO$_2$), and phosphino (—PH$_2$), mono- and di-(C1-C24 alkyl)-substituted phosphino, mono- and di-(C5-C20 aryl)-substituted phosphine. In addition, the aforementioned functional groups may, if a particular group permits, be further substituted with one or more additional functional groups or with one or more hydrocarbyl moieties such as those specifically enumerated above.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O) O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkyl groups are, unless otherwise specified, —R$^{60}$, halo, -O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$$^-$M$^+$, —SO$_3$R$^{70}$, —OSO$_3$R$^{70}$, —OSO$_3$$^-$M$^+$, —OSO$_3$R$^{70}$, —PO$_3$$^{-2}$(M$^+$)$_2$, —P(O)(OR$^{70}$)O$^-$ M$^+$, —P(O)(OR$^{70}$)$_2$, —C(O)R$^{70}$, —C(S)R$^{70}$, —C(NR$^{70}$)R$^{70}$, —OCO$_2$-M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$-M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$-M$^+$, —NR$^{70}$CO$_2$R$^{70}$, —NR$^{70}$C(S)OR$^{70}$, —NR$^{70}$C(O)NR$^{80}$R$^{80}$, —NR$^{70}$O(NR$^{70}$)R$^{70}$ and —NR$^{70}$C(NR$^{70}$)NR$^{80}$R$^{80}$, where R$^{60}$, R$^{70}$, M$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O$^-$)$_2$(M$^+$)$_2$, —P(O)(OR$^{70}$)O$^-$M$^+$, —P(O)(OR$^{70}$)(OR$^{70}$), —O(O)R$^{70}$, —C(S) R$^{70}$, —C(NR$^{70}$) R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S) R$^{70}$, —OC(O) OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O) NR$^{80}$R$^{80}$, —NR$^{70}$C(NR$^{70}$)R$^{70}$ and —NR$^{70}$C(NR$^{70}$) NR$^{80}$R$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

In certain embodiments, a substituent may contribute to optical isomerism and/or stereo isomerism of a compound. Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Unless otherwise specified, reference to an atom is meant to include isotopes of that atom. For example, reference to H is meant to include $^1$H, $^2$H (i.e., D) and $^3$H (i.e., T), and reference to C is meant to include $^{12}$C and all isotopes of carbon (such as $^{13}$C).

The term "lipid" is used broadly herein to encompass substances that are soluble in organic solvents, but sparingly soluble, if at all, in water. The term lipid includes, but is not limited to, hydrocarbons, oils, fats (such as fatty acids and glycerides), sterols, steroids and derivative forms of these compounds. In some embodiments, lipids are fatty acids and their derivatives, hydrocarbons and their derivatives, and sterols, such as cholesterol. Fatty acids usually contain even numbers of carbon atoms in a straight chain (commonly 12-24 carbons) and may be saturated or unsaturated, and can contain, or be modified to contain, a variety of substituent groups. For simplicity, the term "fatty acid" also encompasses fatty acid derivatives, such as fatty or esters. In some embodiments, the term "lipid" also includes amphipathic compounds containing both lipid and hydrophilic moieties.

The term "Acrylic acid derivative" is meant to encompass any convenient derivative of acrylic acid. In certain cases, the acrylic acid derivatives include esters, salts or amides of acrylic acid.

The term "copolymer" is one of the art. It refers to a polymer comprising two or more different monomer units that are polymerized in a process called copolymerization. Since a copolymer comprises at least two different monomer units, copolymers can be classified based on how the monomer units are arranged to form a polymer chain. Those classifications include "alternating copolymers" (in which the monomers units repeat with a highly regular alternating pattern), "periodic copolymers" (in which the monomers units are arranged with a repeating sequence), "statistical copolymers" (in which the sequence of monomer units follows a statistical rule), "random copolymers" (in which the monomer units are attached in a random order), and "block copolymers" (in which two or more homopolymer subunits are linked).

Definitions of other terms and concepts appear throughout the detailed description.

DETAILED DESCRIPTION

Provided herein are compositions including lipids and copolymers in the form of a nanodisc assembly. The subject copolymers include monomer units of styrene and monomer units selected from acrylic acid and an acrylic acid derivative. In certain cases, the copolymer is a copolymer of styrene and acrylic acid. Also provided herein, is an aqueous solution comprising the subject composition. Also provided herein, are methods for producing a nanodisc assembly, including incubation of a lipid and a subject copolymer. Further provided herein, are methods for solubilizing a membrane protein in an aqueous solution, wherein the method includes forming a nanodisc assembly of a lipid bilayer having one or more membrane proteins embedded therein, and a subject copolymer. Also provided are methods of solubilizing a hydrophobic constituent in an aqueous solution, including forming a nanodisc assembly of a lipid, a hydrophobic constituent, and a subject copolymer. In certain cases, the hydrophobic constituent is an active agent, such as a hydrophobic drug.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

Compositions

Aspects of the invention include compositions, e.g., a composition comprising: a lipid; and a copolymer, wherein the copolymer comprises monomer units of styrene, and monomer units selected from acrylic acid, and an acrylic acid derivative, wherein the lipid and copolymer are in the form of a nanodisc assembly.

As used herein, the term "nanodisc assembly" or "nanodisc," refers to at least one lipid bilayer that is stabilized by a synthetic polymer. The synthetic polymer is a copolymer of styrene and acrylic acid or an acrylic acid derivative, e.g., as disclosed herein. The nanodiscs of the present invention are less than one micron in diameter, such as 5-40 nm. The nanodiscs can optionally contain additional lipid components, drugs, membrane proteins, proteins that are not membrane proteins, diagnostic agents, and targeting agents.

Disclosed herein is the use of a subject copolymer, such as a poly(styrene-co-acrylic acid) (AASTY) copolymer, to effectively make regularly sized lipid-polymer disc-shaped particles by incubation of the polymer with lipid bilayers, including living cell membranes. In some embodiments, the polymer is made through Reversible Addition Fragmentation chain Transfer polymerization (RAFT), with subsequently modified end groups. In some embodiments, the ratio of functional groups on the subject copolymers are close to equimolar. The subject nanodiscs are formed upon incubation of the subject copolymer with the lipid bilayers, be it from purified membranes, living cells or organelles. In some cases, the subject nanodiscs formed contain membrane proteins.

In some embodiments, the polymer is capable of solubilizing hydrophobic constituents into aqueous solvents as disc-shaped nanoparticles. In the case of bilayer lipids, the polymer can create nanodiscs of lipids with membrane proteins embedded. These can be used for the study of membrane proteins through techniques such as cryo-EM and Surface Plasmon Resonance. Another application is the solubilization of hydrophobic drugs in aqueous solvents. In certain cases, the subject nanodiscs can be used for dermal delivery of hydrophobic drugs.

The inventors have surprisingly found that the subject copolymers (e.g., AASTY copolymers) in the form of a nanodisc assembly are more effective at solubilizing membrane proteins in lipid nanodiscs than poly(styrere-co-maleic acid) (SMA) copolymers. In certain cases, the subject copolymers is at least 2-fold more effective at solubilizing membrane proteins in lipid nanodiscs than SMA copolymers, such as at least 3-fold, at least 4-fold, at least 5-fold, at least 6-fold, at least 7-fold, at least 8-fold, at least 9-fold or at least 10-fold. The subject copolymers provide a high control of monomer sequence, and high regularity of alternating monomer units. As a result, the subject copolymers are capable of consistently solubilizing membrane proteins from lipid bilayers in appreciable quantities.

Copolymers

As disclosed herein the subject copolymers comprises monomer units of styrene, and monomer units selected from acrylic acid, and an acrylic acid derivative. In certain cases, the copolymer is a highly regular alternating polymer. By highly regular alternating polymer is meant that the copolymer includes two species of monomeric units in alternating sequence.

The neat copolymerization of styrene and acrylic acid exhibits highly alternating behavior (rSTY=0.21, rAA=0.081, see e.g., Harrisson, *Polym. Chem.* (2010) 1, 326-332). Copolymers of styrene and acrylic acid are amenable to conventional batch polymerization, which allows exploration of monomer content and the use of reversible addition—fragmentation chain-transfer (RAFT) to control molecular weight and size distribution. In addition, copolymers of styrene and acrylic acid are amenable to large scale production.

In certain cases, the copolymer is a copolymer of styrene and acrylic acid. In certain cases, the copolymer is a copolymer of styrene and an acrylic acid derivative. Any convenient acrylic acid derivative may find use in the subject copolymers. Example acrylic acid derivatives, without limitation include, acrylate, acylate esters, substituted acrylate esters, acrylamide and N-substituted acrylamide. In certain cases, the acylate esters or acrylamides are substituted with a zwitterionic species, e.g., as disclosed for SMA copolymers in U.S. Patent Application No. 20190062469A1, the disclosure of which is incorporated herein by reference.

In certain embodiments the subject copolymer comprises an acrylic acid, or an acrylic acid derivative (e.g., as described herein) content of from 30% to 70%. In some cases, the copolymer comprises an acrylic acid content of from 30% to 70%, such as 35% to 70%, 40% to 70%, 45% to 70%, 50% to 70%, 55% to 70%, 60% to 70%, or 65% to 70%. In certain cases, the copolymer comprises an acrylic acid content of form 30% to 65%, such as 30% to 60%, 30% to 55%, 30% to 50%, 30% to 45%, 30% to 40%, or 30% to 35%. In certain cases, the copolymer comprises an acrylic acid content of from 35% to 50%. In certain cases, the copolymer comprises an acrylic acid content of about 45%.

In some cases, the copolymer comprises an acrylic acid derivative content of from 30% to 70%, such as 35% to 70%, 40% to 70%, 45% to 70%, 50% to 70%, 55% to 70%, 60% to 70%, or 65% to 70%. In certain cases, the copolymer comprises an acrylic acid derivative content of from 30% to 65%, such as 30% to 60%, 30% to 55%, 30% to 50%, 30% to 45%, 30% to 40%, or 30% to 35%. In certain cases, the copolymer comprises an acrylic acid derivative content of from 35% to 50%. In certain cases, the copolymer comprises an acrylic acid derivative content of about 45%.

In certain embodiments of the subject compositions, the copolymer is described by formula (I):

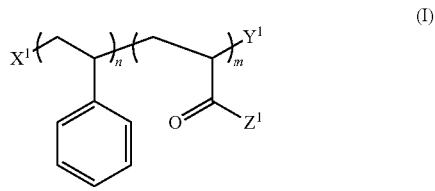

wherein:

$Z^1$ is selected from $OR^1$, and $NR^2{}_2$, wherein $R^1$ is selected from hydrogen, sodium, potassium, alkyl, and substituted alkyl, and each $R^2$ is independently selected from hydrogen, alkyl, and substituted alkyl;

$X^1$ and $Y^1$ are each independently a terminal group; and n and m are each independently an integer from 15-100.

In certain embodiments of a copolymer of formula (I), $Z^1$ is $OR^1$ and $R^1$ is hydrogen, such that the compound of formula (I) is a styrene acrylic acid copolymer.

In certain embodiments of a copolymer of formula (I), $Z^1$ is sodium or potassium, such tat the copolymer is the carboxylate salt. In certain cases the copolymer is formulated as the carboxylate salt to aid in solubilization of the copolymer in water. While the increase in solubility may vary, in some instances the increase (as compared to the copolymer that is not a carboxylate salt) is 2 fold or more, e.g., 5 fold, 10 fold, 25 fold, 50 fold, 100 fold or more. In some cases, the $Z^1$ group is a substituted alkyl group that is charged, e.g., positively or negatively charged. In certain cases, the $Z^1$ group is a substituted alkyl group that is a neutral hydrophilic group. In certain cases, the $Z^1$ group is a substituted alkyl group that is a Zwitterionic species.

In certain embodiments of a copolymer of formula (I), $Z^1$ is $OR^1$ and $R^1$ is alkyl or substituted alkyl, such that the compound of formula (I) is a styrene, acrylic ester copolymer, wherein the ester is optionally substituted.

In certain embodiments of a copolymer of formula (I), $Z^1$ is $NR^2_2$ and $R^2$ is selected from hydrogen, alkyl or substituted alkyl, such that the compound of formula (I) is a styrene, acrylamide copolymer, wherein the acrylamide is optionally substituted an nitrogen. In certain cases, both $R^2$ groups are hydrogen. In certain cases, one $R^2$ is hydrogen and the other $R^2$ group is alkyl or substituted alkyl.

In certain embodiments of a copolymer of formula (I), $X^1$ and $Y^1$ are terminal groups. Any convenient group may find use as a terminal group in copolymers of formula (I). In some embodiments of formula (I), the terminal groups $X^1$ and/or $Y^1$ are each independently a further polymer segment, such as a polyacrylic acid, polyacrylamide, or a polystyrene polymer, or copolymers of any of the foregoing. In certain cases of formula (I), $X^1$ and/or $Y^1$ are each independently a terminal group selected from hydrogen, an alkyl or a substituted alkyl. In certain cases, the terminal groups are groups which are produced as a result of any convenient method of polymerization of the subject co-monomers described herein. In some embodiments of formula (I), $X^1$ and/or $Y^1$ are terminal groups comprising a linker that may include a chemoselective functional group (e.g., as described herein). Any convenient methods of derivatizing or modifying polymers may be utilized to provide for installation of a $X^1$ and/or $Y^1$ group of interest at the terminals of the subject polymers. In certain cases, $X^1$ and/or $Y^1$ group comprises a linked agent, such as a fluorescent dye, or a biomolecule, e.g., biotin, an antibody, etc.

As used herein, the term "chemoselective functional group" refers to chemoselective reactive groups that selectively react with one another to form a covalent bond. Chemoselective functional groups of interest include, but are not limited to, thiol groups, thiols and maleimide or iodoacetamide, as well as groups that can react with one another via Click chemistry, e.g., azide and alkyne groups (e.g., cyclooctyne groups). Chemoselective functional groups of interest, include, but are not limited to, thiols, alkyne, a cyclooctyne, an azide, a phosphine, a maleimide, an alkoxyamine, an aldehyde and protected versions thereof, and precursors thereof. In certain embodiments, the chemoselective functional group is a thiol.

In some embodiments of a copolymer of formula (I), $X^1$ is selected from, alkyl, substituted alkyl, nitrile, hydroxy, carboxyl, and halogen. In certain embodiments of a copolymer of formula (I), $X^1$ is selected from, alkyl and substituted alkyl. In some cases, $X^1$ is substituted alkyl, and the substituent is selected from one or more of, nitrile, hydroxy, carboxyl, and halogen. In certain cases, $X^1$ is an alkyl group including a nitrile substituent. In certain cases, $X^1$ is an alkyl group including a hydroxy substituent. In certain cases, $X^1$ is an alkyl group including a carboxyl substituent. In certain cases, $X^1$ is an alkyl group including a halogen substituent.

In certain embodiments of a copolymer of formula (I), $X^1$ is of the formula (X-I):

(X-I)

wherein:

$R^3$ and $R^4$ are each independently selected from hydrogen, alkyl, and substituted alkyl. In certain cases of formula (X-I), $R^3$ and $R^4$ are both methyl.

In some embodiments of a copolymer of formula (I), $Y^1$ is selected from, alkyl, substituted alkyl, nitrile, hydroxy, carboxyl, halogen, thiol, substituted thiol, acyl, and substituted acyl. In certain embodiments of a copolymer of formula (I), $Y^1$ is selected from, alkyl and substituted alkyl. In some cases, $Y^1$ is substituted alkyl, and the substituent is selected from one or more of, alkyl, nitrile, hydroxy, carboxyl, and halogen, thiol. In certain cases, $Y^1$ is an alkyl group including a nitrile substituent. In certain cases, $Y^1$ is an alkyl group including a hydroxy substituent. In certain cases, $Y^1$ is an alkyl group including a carboxyl substituent. In certain cases, $Y^1$ is an alkyl group including a halogen substituent. In certain cases, $Y^1$ is an alkyl group including a thiol substituent. In certain cases, $Y^1$ is an alkyl group including an acyl substituent.

In certain embodiments of a copolymer of formula (I), $Y^1$ is selected from, nitrile, hydroxyl, carboxyl, halogen, thiol, substituted thiol, acyl, and substituted acyl. In certain cases, $Y^1$ is a nitrile group. In certain cases, $Y^1$ is hydroxyl. In certain cases, $Y^1$ is carboxyl. In certain cases, $Y^1$ is a halogen, e.g., Cl, F, I or Br. In certain cases, $Y^1$ is acyl or substituted acyl.

In certain cases, $Y^1$ is thiol or substituted thiol. In certain cases, $Y^1$ is a thiol or substituted thiol that is amenable to conjugation to a fluorescent dye or a biomolecule of interest, e.g., through maleimide chemistry. In certain cases, the biomolecule is a biotin moiety.

In certain embodiments of a copolymer of formula (I), $Y^1$ is of the formula (Y-I) or (Y-II):

(Y-I)

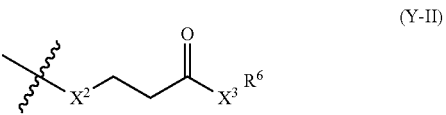

(Y-II)

wherein:

$R^5$ and $R^6$ are each independently selected from hydrogen, alkyl, and substituted alkyl; and $X^2$ and $X^3$ are each independently selected from S and O.

In certain embodiments of formula (Y-I), $R^5$ is hydrogen. In certain cases, $R^5$ is alkyl or substituted alkyl. In certain embodiments of formula (Y-II), $X^2$ and $X^3$ are both oxygen. In certain cases, $X^2$ and $X^3$ are both sulfur. In certain cases, $X^2$ is S and $X^3$ is O. In certain cases, $X^2$ is O and $X^3$ is S. In certain cases, $R^6$ is hydrogen. In certain cases, $R^6$ is alkyl. In certain cases, $R^6$ is substituted alkyl.

In certain embodiments of formula (Y-II), the compound is of the formula (Y-III):

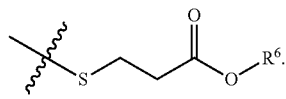
(Y-III)

In certain embodiments of a copolymer of formula (I), n and m are each independently an integer from 15-100, such as 20-100, 30-100, 40-100, 50-100, 60-100, 70-100, 80-100, or 90-100. In certain cases, n and M are each independently an integer from 15-50, such as 20-50, 25-50, 30-50, 35-50, 40-50, or 45-50.

In some embodiments of formula (I), one or more terminal groups (e.g. $X^1$ and/or $Y^1$) are introduced by reversible addition-fragmentation chain-transfer (RAFT) polymerization in the preparation of the copolymer of formula (I) using a chain transfer agent. In some cases, the chain transfer agent is 2-(Dodecylthiocarbonothioylthio)-2-methylpropionic acid (DDMAT). In another aspect, one or more end groups of the copolymer of formula (I) is introduced by RAFT chain transfer agents that are cleaved or converted to other chemical groups, including but not limited to thiol, hydroxyl, carboxyl, amine, and alkyl groups. In another aspect, the copolymer of formula (I) is prepared via other polymerization methods selected from at least one of anionic polymerization, cationic polymerization, conventional free radical polymerization, or other types of controlled/living free radical polymerization such as atom transfer radical polymerization (ATRP), and nitroxide mediated polymerization (NMP). It will be understood that any convenient means can be utilized to facilitate the preparation of copolymers of formula (I).

In certain embodiments of a copolymer of formula (I), n and m are the same. In certain cases, n and m are integers that differ by less than 50, such as less than 40, less than 30, less than 20, less than 10, less than 5, or even less. In certain cases, n is greater than m. In certain cases n is up to 50% greater than m, such as up to 40%, up to 30%, up to 20%, or up to 10% greater than m. In certain cases, m is greater than n. In certain cases m is up to 50% greater than n, such as up to 40%, up to 30%, up to 20%, or up to 10% greater than n.

In certain embodiments of a copolymer of formula (I), the molecular weight of the copolymer is from 2 kDa to 15 kDa. In certain cases, the molecular weight is from 2 kDa to 12 kDa, such as 2 kDa to 10 kDa, 2 kDa to 8 kDa, 2 kDa to 6 kDa, or 2 kDa to 4 kDa. In certain cases, the molecular weight of the copolymer is from 3 kDa to 8 kDa. In certain cases, the molecular weight of the copolymer is from 7 kDa to 8 kDa.

In certain embodiments of the subject compositions, the copolymer is described by formula (II):

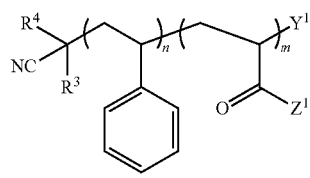
(II)

wherein:
$R^1$, $R^3$, and $R^4$ are each independently selected from hydrogen, alkyl, and substituted alkyl;
$Y^1$ is selected from:

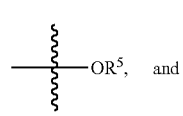
(Y-I)

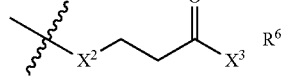
(Y-II)

wherein:
$R^5$ and $R^6$ are each independently selected from hydrogen, alkyl, and substituted alkyl; and
n and m are each independently an integer from 15-100.

In certain embodiments of the copolymer of formula (II), the copolymer is further described by the formula (III) or (IV):

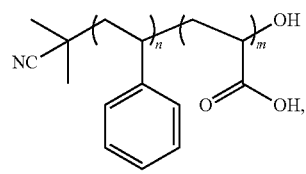
(III)

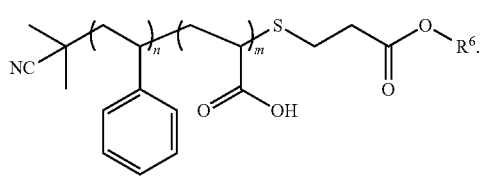
(IV)

Lipids

As disclosed herein the subject composition comprises lipids. Any convenient lipid can find use in the subject compositions. Subject Lipids can include fats, waxes, steroids, cholesterol, fat-soluble vitamins, monoglycerides, diglycerides, triglycerides, phospholipids, sphingolipids, glycolipids, cationic or anionic lipids, derivatized lipids, and the like. Lipids can form micelles, monolayers, and bilayer membranes. In certain cases, the lipids can be derived from purified membranes, living cells or organelles.

The subject lipids can self-assemble in combination with other components, e.g., subject copolymers, as described above, to form a nanodisc assembly.

In certain cases, the lipid is a membrane-forming polar lipid, which denotes lipids having a highly polar head portion attached to a nonpolar hydrophobic tail, generally composed of a pair of relatively long hydrocarbon chains, such that in aqueous media the lipid molecules tend to associate and form membrane structures at interfaces, possibly as lipid monolayers or bilayers.

In some embodiments, the lipid comprises a phospholipid. Exemplary phospholipids include those from natural sources, synthetic sources, saturated, unsaturated, mixed acyl, diether and lyso, for example, phosphatidylcholine, phosphatidic acid, phosphatidylethanolamine, phosphatidylglycerol, phosphatidylserine, phosphatidylinositol, phosphatidylinositolphosphate, or cardiolipin. In certain embodiments, polar lipids used in connection with the present disclosure are phospholipids based on glycerol in the form of phosphatidic acid derivatives in which the non-polar acyl ester groups contain between 8 and 25 carbon atoms. The acyl ester are selected from lauryl, palmitoyl and myristoyl, and the polar head of the molecule can be provided by the phosphate group with a choline substituent, i.e. the lipid can be a phosphatidylcholine (POPC).

In some embodiments polar lipids, are selected from the phospholipids, sphingosine or a ceramide from which may be derived the phospholipid sphingomyelin.

In some embodiments, the lipid is a sphingolipid. Exemplary sphingolipids include those from natural sources, synthetic sources, phosphorylated, unphosphorylated, methylated), for example, sphingosines, ceramides, sphingomyelin, gangliosides, glycosphingolipids, phosphosphingolipids, or phytosphingosine.

In some embodiments, the lipid is a sterol. Exemplary sterols include those from natural sources, synthetic sources, substituted oxysterols and derivatives, for example, cholesterol or trihydroxycholestanoic acid. In certain embodiments, the lipid is Coenzyme A: free acid, acylated, saturated or unsaturated.

In certain embodiments, the lipid is a neutral lipid. Neutral lipids include, for example, diacylglycerol, glycosylated diacylglycerols, prostaglandins, prenols, N-acyl glycine, and very long chain fatty acids. In a particular embodiment, the lipid is diacylglycerol or PGF1a.

In some embodiments the polar lipid is a fluorescent lipid. In some cases, the lipid is 1,2-dimyristoyl-sn-glycero-3-phosphoethanolamine-N-(lissamine rhodamine B sulfonyl) (ammonium salt) (also referred to herein as LisRhod PE lipid).

In some embodiments, the lipid is Soy polar lipid extract (Soy PLEx). In some cases, the lipid is E. coli polar lipid extract (E. coli PLEx).

Nanodisc Assembly

As disclosed herein the composition is in the form of a nanodisc assembly. The term "nanodisc" or "nanodisc assembly as used herein refs to a disc shaped nanostructure, including lipids (e.g., native bilayers) encompassed by a copolymer, which forms a belt-like structure around the said lipids. The hydrophobic face of the copolymer serves to sequester the hydrocarbon tails of the lipids away from solvent. The resulting disc shaped particle is aqueously soluble and stable. A subject nanodisc assembly is depicted in FIG. 3.

In certain cases, the nanodisc assembly has a diameter of from 5 to 40 nm. In certain cases, the nanodisc assembly has a diameter of from 5 to 50 nm, such as 5 to 45 nm, 5 to 40 nm, 5 to 35 nm, 5 to 30 nm, 5 to 25 nm, 5 to 20 nm, 5 to 15 nm, or 5 to 10 nm. In some cases, the a nanodisc assembly has a diameter of from 10 to 50 nm, such as 15 to 50 nm, 20 to 50 nm, 25 to 50 nm, 30 to 50 nm, 35 to 50 nm, 40 to 50 nm, or 45 to 50 nm.

In certain case the nanodisc assembly includes a membrane protein. In certain cases, the membrane protein is surrounded by a native lipid bilayer, and the nanodisc assembly is a native nanodisc assembly. By "native nanodisc assembly," or "native lipid nanodisc," it is meant that a particular membrane protein has been extracted from cells without ever separating it from its immediate membrane environment. The formation of native lipid nanodiscs allows for the study of membrane proteins, such as structural characterization of membrane protein-lipid interactions.

Accordingly, it some embodiments, the subject copolymer can be used to form nanodiscs of lipids with membrane proteins embedded.

In certain cases, there is provided an aqueous solution comprising a subject composition in the form of a nanodisc assembly. In certain embodiments the composition includes a hydrophobic moiety within the nanodisc assembly. In certain embodiments, the hydrophobic moiety is a drug, and nanodisc assembly assists in the solubilization of the hydrophobic drug in the aqueous solution.

Methods

As summarized above, provided herein are methods of producing a subject nanodisc assembly. Aspects of the methods include, producing a nanodisc assembly, the method comprising: incubation of a lipid and a copolymer, wherein the copolymer comprises monomer units of styrene, and monomer units selected from acrylic acid and an acrylic acid derivative. Aspects of the methods include incubation of a lipid and a subject copolymer (e.g., as described herein).

In certain embodiments of the methods, the copolymer is of any one of formulae (I)-(IV).

In certain embodiments of the methods, the lipid is as described herein. In certain embodiments of the methods, the lipids comprise lipids from purified membranes, living cells or organelles. In some embodiments the lipids are from purified membranes. In some embodiments, the lipids are form living cells. In some cases, the lipids are from organelles. In some cases, the lipid is a single pure component. In some cases, the pure lipid is of synthetic or semi-synthetic origin. In other embodiments, the lipid is a mixture of components. In some cases, the mixture of lipids is of natural origin, e.g., obtained by extraction and purification by means known to those skilled in the art.

In some embodiments of the methods, the nanodisc assembly includes one or more membrane proteins. Membrane proteins that find use in the subject methods include integral membrane proteins, i.e. any protein that crosses, or is embedded or integrated into such membranes, including G-protein coupled receptors (GPCRs), ion channels and transporters. Approximately one third of eukaryotic proteins are associated with membranes in this way. Integral membrane proteins typically have one or more regions which are hydrophobic and lie within the hydrophobic interior of the membrane bilayer, and one or more regions which are hydrophilic and extend out from the membrane. The hydrophilic regions may lie on either or both sides of the membrane. In some cases, the one or more membrane proteins are soluble at a pH<7.0. In some cases, the one or more membrane proteins are soluble in the presence of cations. In some cases, the one or more membrane proteins are adapted for the determination of acidification-induced rhodopsins spectral shifts, activation of ion channels (such as KcsA), or measurement of ATPases. In another embodiment, the one or more membrane proteins are rhodopsins, ion pumps, ATP-binding cassette proteins. In some cases, the one or more membrane proteins are at least one of P-type, F-type, V-type, or ABC ATPases.

Aspects of the methods include, solubilizing a membrane protein in an aqueous solution, the method comprising forming a nanodisc assembly of a lipid bilayer having one or more membrane proteins embedded therein; and a copolymer, wherein the copolymer comprises monomer units of styrene, and monomer units selected from acrylic acid and an acrylic acid derivative.

In certain embodiments, the subject compositions increase the aqueous solubility of the membrane protein by at least 2-fold, at least 3-fold, at least 4-fold, at least 5-fold, at least 6-fold, at least 7-fold, at least 8-fold, at least 9-fold, or at least 10-fold compared to the solubility of the membrane protein in the absence of the subject composition.

Accordingly, the subject compositions may be in the form of an aqueous solution. In some cases, the subject composition is in the form of a stable clear aqueous solution. In some cases, for ease of transportation and handling, once prepared, the compositions may be freeze-dried to form a dry powder which has the benefits of being lower in both volume and weight. In one embodiment of the present invention the composition is in the form of an aqueous solution. In a further embodiment of the present invention the composition is in freeze-dried form (for example as a powder, resin or flake). Aqueous solutions include aqueous semi-solids such as gels. In one embodiment, the subject composition is in the form of an aqueous solution comprising 0.001-10% by weight of the compositions disclosed herein (the percentage being determined by the dry weight of composition of the invention relative to the total weight of composition and water). In some cases, the subject composition is in the form of an aqueous solution comprising 10-20% by weight of the compositions disclosed herein. In some cases, the subject composition is in the form of an aqueous solution comprising greater than 20% by weight of the compositions disclosed herein.

Compositions of the present invention may suitably be prepared by mixing a solution of a subject copolymer (e.g., as described herein), with an aqueous emulsion containing lipid, and if necessary adjusting the pH of the resulting mixture such that the polymer/lipid nanodisc assemblies form.

The polymer solution may be prepared by dissolving the polymer in water, optionally with stirring and heating. The lipid emulsion may be prepared by mixing dried lipid with water, optionally under stirring and heating (suitably to a temperature above the phase transition temperature of the lipid component), followed by homogenisation. Suitably the polymer solution and lipid emulsion are mixed by the addition (e.g. the slow addition) of lipid emulsion to the polymer solution, optionally together with heating.

The pH of solutions may be adjusted using acids or bases as appropriate. Compositions for use in the fields of cosmetics or pharmaceuticals will typically utilize acids and/or bases which are physiologically acceptable. Physiologically acceptable acids include hydrochloric acid. Physiologically acceptable bases include sodium or potassium hydroxide, suitably sodium hydroxide.

Aspects of the methods also include, solubilizing a hydrophobic constituent in an aqueous solution, the method comprising forming a nanodisc assembly of: a lipid; a hydrophobic constituent; and a copolymer, wherein the copolymer comprises monomer units of styrene, and monomer units selected from acrylic acid and an acrylic acid derivative.

In certain cases of the method of solubilizing a hydrophobic constituent, the hydrophobic constituent is an active agent (e.g., a hydrophobic drug).

In certain embodiments, the subject compositions increase the aqueous solubility of a hydrophobic constituent, e.g., an active agent, by at least 2-fold, at least 3-fold, at least 4-fold, at least 5-fold, at least 6-fold, at least 7-fold, at least 8-fold, at least 9-fold, or at least 10-fold compared to the solubility of the hydrophobic constituent in the absence of the subject composition.

Accordingly, the subject compositions may find use as solubilizing agents. Solubilizing agents may be of use as formulating aids, solubilizing active agents which have poor aqueous solubility (for example aqueous solubility of less than 1% w/w, suitably less than 0.1% w/w or less than 0.01% w/w). Solubilizing agents may also be of use as carriers for active agents which preferentially partition into the solubilizing agent (for example, active agents which partition into octanol as opposed to water). The active agent may for example be a medicament for the treatment or prevention of a medical disorder, or alternatively may be a cosmetic agent or an agent which is applied for cosmetic purposes.

Active agents having poor aqueous solubility include the oil-soluble vitamins (including vitamins A, D, E and K) and oil soluble derivatives of water soluble vitamins (including vitamin C), which are frequently applied to the skin as part of water-in-oil or oil-in-water emulsions as antioxidants, depigmenting agents, moisturizers, collagen stimulators, anti-aging, anti-wrinkle and anti-inflammatory agents.

The vitamin A family includes retinol, retinol palmitate, retinol acetate, and related retinoids, and also pro-vitamin A, such as β-carotene. Oil-soluble derivatives of vitamin C include ascorbyl palmitate, ascorbyl dipalmitate and ascorbyl tetraisopalmitate (in particular ascorbyl palmitate and ascorbyl dipalmitate). Vitamin D and its derivatives include cholecalciferol/calcitriol (vitamin D3), calcipotriol and tacalcitol (in particular cholecalciferol), which may be used in the treatment of psoriasis. Vitamin K series, including K1 (phytonadione), may be used in the treatment of bruised skin and in the repair of capillary damage. 7-dehydrocholesterol is a pre-cursor for vitamin D.

A large number of active agents demonstrating a poor aqueous solubility are based around a triterpenoid or steroidal nucleus. Many of these agents have potent biological activity and are widely used in cosmetics and pharmaceuticals.

Oil-soluble actives based upon a triterpenoid structure include natural extracts (for example from *Centella asiatica* (Hydrocotyl), such as TECA, asiaticoside, asiatic acid and madecassic acid (in particular TECA, alternatively asiaticoside), which are of use in regulating and activating collagen synthesis; or liquorice extracts such as glabridin, which is of use as an anti-tyrosinase and anti-microbial, and licochalcone A, which is of use as an inhibitor of 5-alpha-reductase and as an anti-microbial). Additional actives include extracts from *Aesculus* (Horse chestnut). Other actives include escin (a triterpenoid) and esculoside (esculin, a coumarin). Further glycoside actives include extracts from Ruscus (Butcher's broom), including ruscogenin and neuroruscogenin. Triterpenoid extracts of Boswellia (Frankincense) including Boswellin® CG from Sabinsa Corporation USA are also examples of actives in this class. Other oil-soluble actives based upon a steroidal structure include those used to treat inflammatory conditions (such as hydrocortisone, clobetasone butyrate, hydrocortisone butyrate, clobetasol propionate, fluticasone propionate and dexamethasone, in particular hydrocortisone, clobetasone butyrate, hydrocortisone butyrate, clobetasol propionate and dexamethasone) and hormones (such as testosterone, oestrogen and oestrogens). Additional steroidal compounds include dexamethasone acetate anhydride, hydrocortisone acetate and cortisone acetate. Steroidal like compounds include cholesterol and cholesterol potassium sulphate which may, for example, be used in moisturizing.

Other active agents include soy isoflavones; liquorice extracts, such as Licorice CG from Sabinsa Corporation USA, P-U and PT-40 from Maruzen Pharmaceuticals Co. Ltd. Japan.

Endogenous skin lipids, including ceramides (e.g. ceramide IIIA) have poor aqueous solubility and are of use as skin moisturisers and whitening agents. Other ceramides include ceramide IIIB and synthetic ceramides.

Other relatively oil-soluble actives include lawsone (2-hydroxy-1,4-naphthoquinone), natural henna extract of Lawsonia alba, caffeine and minoxidil.

Antimicrobial active agents include: anti-bacterials, such as erythromycin, neomycin (e.g. as the sulphate); anti-fungals, such as ciclopirox olamine, piroctone olamine (each of which are examples of pyridone antifungals), clotrimazole, fluconazole, econazole, ketaconazole and nystatin (in particular piroctone olamine, clotrimazole, ketaconazole and nystatin).

Oil-soluble derivatives of active agents which have a peptide structure include Matrixyl™ (palmitoyl-KTTKS, which downregulates collagenase and therefore increases collagen production) and Argireline® (acetyl hexapeptide-3, which inhibits acetylcholine binding, decreasing the strength of neuromuscular signals and thus decreasing muscle contraction).

Further oil-soluble active botanical extracts include rosmarinic acid and green tea extract from Sabinsa Corporation USA, nettle extracts and ginkgo extracts.

Cosmoperine® from Sabinsa Corporation USA is an oil-soluble penetration enhancer.

An oil-soluble anti-oxidant is NDGA (nordihydroguaiaretic acid) from Whyte Chemicals UK.

Another class of active agents includes sunscreens. Exemplary sunscreens include octyl methoxycinnamate, benzophenone 3,3-benzylidene camphor, avobenzene, para-aminobenzoic acid (PABA) and galanga (ethylhexyl para-methoxy cinnamate).

A still further class of active agents is essential oils including a melaleucole oil and peppermint oil and fragrances including Unisex Bouquet (AFL-3607/A), Apricosal (AFL-3607/E) and Fougere (AFL-3607/D) supplied by Arriva Fragrances, UK.

A still further class of active agents is coolants and natural moisturizing agents such as Questice CQ U/A (Menthyl PCA) supplied by Quest International, UK. Another class of active agents is dyes.

The quantity of active agent which may be combined with and solubilized in the compositions (e.g., as described herein) can be in the range of 0.001-50% of the weight of polymer and lipid, such as in the range of 0.001-25%, such as 1-20%, 1 to 15% or 1 to 10%.

Active agents may be conveniently incorporated into the compositions of the present invention by the addition of the active agent to the lipid prior to the preparation of the aqueous lipid emulsion, and before the emulsion and polymer solution are mixed.

In an analogous manner to any of the foregoing methods, aqueous formulations of the present invention (which comprise an active agent) may generally be freeze-dried and reconstituted as necessary. As such, also provided is a formulation comprising a subject composition, and which further comprises an active agent, which is in freeze-dried form (for example as a powder, resin or flake, in particular powder or flake).

In general a formulation of the present invention may be incorporated into a cosmetic or pharmaceutical preparation which is tailored to suit the particular purpose, manner of use and mode of administration. Formulations may be mixed with one or more cosmetic or pharmaceutically acceptable carriers or excipients (anti-oxidants, preservatives, viscosity modifiers, colorants, flavourants, perfumes, buffers, acidity regulators, chelating agents, or other excipients), and optionally with other therapeutic ingredients if desired. Such preparations may be prepared by any of the methods known in the art, and may for example be designed for inhalation, topical or parenteral (including intravenous, intra-articular, intra-muscular, intra-dermal and subcutaneous) administration.

Kits

Aspects of the invention further include kits for use in practicing the subject methods and compositions. The copolymers of the invention can be included as reagents in kits for use in, for example, the methodologies described above.

A kit can include a copolymer or a nanodisc (e.g., as described herein); and one or more components selected from the group consisting of a lipid, a buffer, a solvent, a standard and instructions for use.

The one or more components of the kit may be provided in separate containers (e.g., separate tubes, bottles, or wells in a multi-well strip or plate).

The copolymers and nanodiscs of the kits may be provided in a liquid composition, such as any suitable buffer. Alternatively, the copolymers and nanodiscs of the kits may be provided in a dry composition (e.g., may be lyophilized), and the kit may optionally include one or more buffers for reconstituting the dry compound. In certain aspects, the kit may include aliquots of the copolymer or nanodisc provided in separate containers (e.g., separate tubes, bottles, or wells in a multi-well strip or plate).

In addition, one or more components may be combined into a single container, e.g., a glass or plastic vial, tube or bottle. In certain instances, the kit may further include a container (e.g., such as a box, a bag, an insulated container, a bottle, tube, etc.) in which all of the components (and their separate containers) are present. The kit may further include packaging that is separate from or attached to the kit container and upon which is printed information about the kit, the components of the and/or instructions for use of the kit.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, portable flash drive, etc., on which the information has been recorded. Yet another means that may be present is a website address which may be used via the Internet to access the information at a removed site. Any convenient means may be present in the kits.

Utility

The subject compositions, methods and kits find use in a variety of applications, including structural characterization of membrane protein-lipid interactions, solubilization of hydrophobic constituents, e.g., an active agent, and the delivery of hydrophobic active agents to a subject in need of treatment.

Compositions as described herein can be particularly suitable for the delivery of active agents to the skin. When delivering active agents to the skin it is generally important that the particle size be less than that of the lipid interstices found between the corneocytes within the outer layer of the skin, in order for the material to be adequately absorbed into the stratum corneum. The inter-corneocyte interstices have a thickness in the region of 50-100 nm, hence, particles (for example the nanodisc assemblies of the present invention) should desirably to be sized less than 100 nm, especially less than 50 nm and more particularly less than 25 nm in order to be absorbed efficiently. Hydrophilic pores/spaces between the corneocytes and the lipid lamellae layers within the skin are substantially smaller than the lipid interstices, starting in the order of 0.4 nm but having an ability to enlarge to around 20-30 nm in diameter (Cevc, G Advanced Drug Delivery Reviews 2004 56:675-711). The nanodisc assemblies described herein may be well suited to penetrating the inter-corneocyte lipid layer and also the hydrophilic pores, and could therefore be used to deliver oily materials e.g. active agents. Since the macromolecular assemblies may be trapped within the stratum corneum, they may act as reservoirs for active agents to enable sustained release into the deeper layers of the skin and thereby provide a distinct therapeutic profile. Advantageously, this could improve product efficacy, reduce the number of applications and quantity of active agent required, and would be more convenient for the consumer or patient.

Preparations for topical application may include, for example, anti-oxidants (e.g. alpha-tocopherol, butylated hydroxyanisole (BHA) or butylated hydroxytoluene (BHT)), preservatives (e.g. 2-phenoxyethanol, sorbic acid or parabens), viscosity modifiers (e.g. water soluble gums and resins, such as xanthan gum, or lightly cross-linked synthetic polymers such as carbopols), colorants, flavorants, perfumes, buffers, acidity regulators, chelating agents (e.g. such as EDTA, sodium edetate, disodium edetate or calcium disodium edetate), penetration enhancers and anti-tack agents. Suitable carbomers include Carbopol®980 and Ultrez® 20.

Preparations for topical application may be incorporated into hydrogel patches (i.e. 3-dimensional gels of fixed structure). Application utilizing hydrogels may be advantageous in that: (i) the hydrogel patch may act as a convenient repository for prolonged administration and/or (ii) the hydrogel patch may provide a quantifiable dosage form, such that the quantity of active agent administered can be effectively controlled.

The subject compositions can also find use as a solubilizing agent, for example in the solubilization of an active agent (e.g. an oil soluble vitamin or oil soluble vitamin derivative, an agent having triterpenoid or steroidal nucleus, or an oil soluble peptide). Other active agents which may be solubilized include terpenoids.

The subject compositions can also find use as a means of solubilizing membrane peptides or proteins for the investigation of their structure. A need has been identified for solubilizing agents that can be used for solubilizing membrane peptides and proteins (including integral, membrane tethered or membrane associated proteins, for example drug receptor proteins), within phospholipid membranes in such a way as to retain their native conformation and thereby to enable their structure to be investigated (e.g. by NMR spectroscopy).

In addition to structural investigations, the subject compositions may also find use in establishing the interactions of membrane proteins and peptides with other species. Such other species may also be membrane peptides and proteins. In the case of membrane receptors such other species include ligands and ligand fragments (e.g. agonists and antagonists). In the case of enzymes, such other species may be ligands and ligand fragments (e.g. substrate(s) and inhibitors). Other membrane bound or membrane associated molecules which may be the subject of investigations include glycolipids.

The subject compositions may also find use in solubilizing peptides or proteins which are immunogenic in nature (e.g. antigens). Alternatively, it may be noted that WO95/11700 discloses an oil-in-water submicron emulsion (SME) for use as a vaccine adjuvant for enhancing immunogenicity and improving the immune response of antigens in vaccines. Compositions of the present invention may also be of use as particulate vaccine adjuvants.

Furthermore, the subject compositions may find use in the treatment of medical conditions affecting mucosal surfaces, e.g. for ophthalmic use such as in the treatment of the condition known as "dry eye" syndrome, and for lubricating biological membranes (e.g. synovial). The tear film has a coating of phospholipids, which are necessary for the formation of a stable tear film. Diseases where the tear film is deficient may potentially be treated by the addition of an aqueous phospholipid solution, such as an aqueous solution of the compositions of the present invention.

The subject compositions may also find use in lubricating phospholipids to treat the surfaces of articulated joints in connection with arthritic conditions or to lubricate surfaces of medical devices and prostheses, e.g. artificial joints and contact lenses, that are fitted into or on the body, or to prevent focal adhesions between tissues such as those that may occur during surgical procedures. Compositions of the present invention may be of use in this regard (e.g. by intra-articular injection).

The compositions of the invention may also find use in the delivery of active agents locally to the lung or, via the highly permeable membranes lining the deep lung, into the systemic circulation. The similarity between the phospholipid compositions of the invention and the surfactant fluid lining the internal alveolar and bronchial surfaces of the lung may ensure that the compositions of the invention are suited to deliver active agents to the lung, especially the deep lung, or to act as a means of delivering phospholipid to the lung for the treatment of neonatal or adult respiratory distress syndrome, a condition characterized by insufficient levels of native lung surfactant or phospholipids. Delivery to the lung may be by aerosol or by nebulization.

The following example(s) is/are offered by way of illustration and not by way of limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle &

Griffiths, John Wiley & Sons 1998), the disclosures of which are incorporated herein by reference. Reagents, cloning vectors, cells, and kits for methods referred to in, or related to, this disclosure are available from commercial vendors such as BioRad, Agilent Technologies, Thermo Fisher Scientific, Sigma-Aldrich, New England Biolabs (NEB), Takara Bio USA, Inc., and the like, as well as repositories such as e.g., Addgene, Inc., American Type Culture Collection (ATCC), and the like.

Introduction

Herein it is shown that functional polymers poly(acrylic acid-co-styrene) (AASTY) is a highly functional copolymer for use in nanodisc formation. The neat copolymerization of AA and STY exhibits highly alternating behavior (rSTY=0.21, rAA=0.081, (Harrisson et al. Polym. Chem. 2010, 1, 326-332)). The AASTY copolymer is amenable to conventional batch polymerization, which allows exploration of monomer content and the use of RAFT to control molecular weight and size distribution. In addition, the AASTY copolymer is scalable.

Herein, we present seven exemplary AASTY polymers composed by different ratios of acrylic acid to styrene, whilst keeping the molecular weight comparable, while also testing the effect of the presence of the dodecyl terminal group. These are tested for different lipid mixtures in the absence of proteins, as well as on whole mammalian cells modified to express a GFP coupled membrane protein.

Example 1: Preliminary AASTY Polymer Study

To test whether the AASTY polymers were effective in forming nanodiscs, a small test set of polymers were synthesized, designated A, B and C, varying the initial [AA]:[STY] composition 25:75, 35:65, and 45:55, respectively.

Based on our previous study, we hypothesized that a gradient copolymer in the 3-4 kDa molecular weight range might prove effective (Smith et al. Biomacromolecules (2017), 18, 3706-3713). Moreover, this modest copolymer size can allow us to assess whether retaining the dodecyltrithiocarbonate end-group from the RAFT polymerization in the copolymer has an effect on protein solubilization. The effect from the dodecyltrithiocarbonate end-group is exacerbated in a small copolymer, as it will constitute a higher weight fraction.

The relative reactivity of a propagating radical in a copolymerization for reacting with a monomer identical to the terminal monomer on the propagating chain, versus the rate of addition to the other monomer, denotes the reactivity ratio. These ratios are defined for both monomers for a given copolymerization.

Accordingly, A, B and C were synthesized in the 3-4 kDa range. The reactivity ratios for AASTY dictate that a batch controlled radical polymerization will have a gradient structure if not at an azeotropic composition, which was confirmed using Compositional Drift analysis in conjunction with monomer consumption by NMR (FIG. 1A and FIG. 1B) (Smith et al. Acs Macro Lett 2019, 8, 36-40). A and B exhibited a higher content of AA than the mol fraction of the feed, while C was close enough to the azeotropic monomer composition as to not have a discernable gradient arise, i.e. the initial AA is equal to the AA in the final polymer (FIG. 1A).

The Compositional drift analysis reveals that A has a wide distribution of STY run lengths, though virtually all AA is found with a run length of 1 i.e., two acrylic acids are very unlikely to appear in sequence along the monomer chain. (see, e.g., FIG. 1C). Plots of polymers B and C show that increasing the initial AA, increases the fraction of STY of run length 1, with only a slight increase in AA with run lengths greater than 1.

Figure 1D:
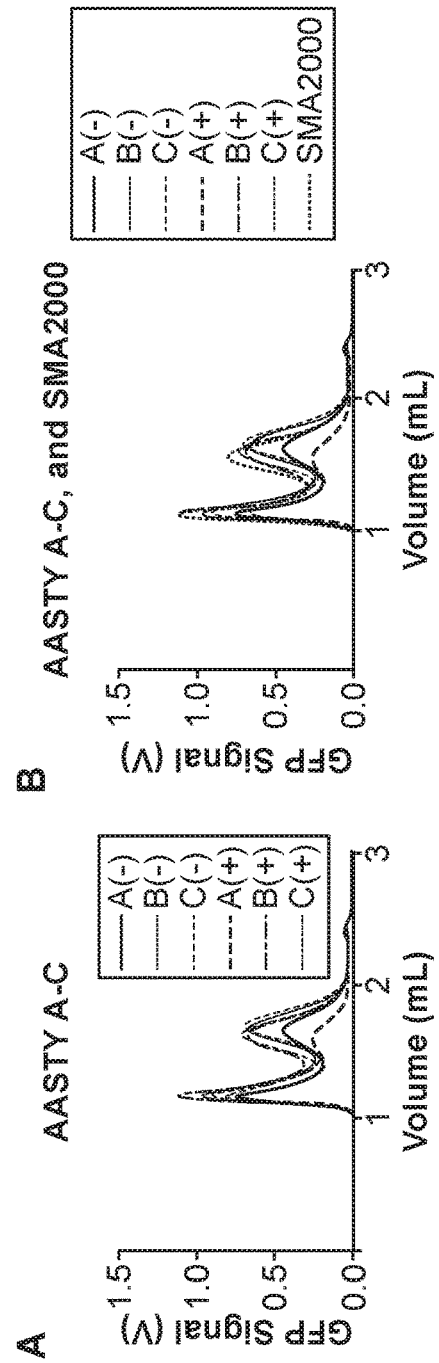
FIG. 1D, panel A illustrates fluorescent size exclusion chromatography (FSEC) of human transient receptor potential melastatin type 4 (hTRPM$_4$) fused with an N-terminal green fluorescent protein (GFP) tag extracted with poly (acrylic acid-co-sytrene (AASTY) polymers A, B and C with (+) and without (−) dodecyltrithiocarbonate end group.

A small gradient copolymer could exhibit a detergent-like bimodal presentation of amphiphilicity, where one end of the polymer is predominantly hydrophilic, and the other hydrophobic. Furthermore, this enabled ascertaining whether the dodecyltrithiocarbonate end-group influenced protein solubilization, with the rationale being that a smaller polymer would have a higher weight fraction of the end-group, exacerbating a possible effect. In order to test the solubilizing effects of the AASTY polymers and their ability to form nanodiscs, we carried out fluorescent size-exclusion chromatography (FSEC) using a mammalian integral membrane protein as our test system. AASTY-A, -B and -C were added to $HEK_{293}F$ cells overexpressing the human transient receptor potential melastatin type 4 ($hTRPM_4$) fused with an N-terminal eGFP tag and the cleared lysate was injected onto a Superose 6 Increase size-exclusion chromatography (SEC) column (FIG. 1D, panel A). Testing AASTY-A-C with (+) and without (−) the dodecyltrithiocarbonate end-group, showed that all six variants AASTY polymers can reconstitute $hTRPM_4$ directly from membranes, however, AASTY-A seemed to be impeded by the extra STY content relative to the AASTY-B and -C polymers in addition to the dodecyltrithiocarbonate end-group (FIG. 1A and FIG. 1D, panel A). Considering that AASTY-A is the most lipophilic polymer of the three, it is likely that the dodecyltrithiocarbonate end-group makes it too lipophilic to effectively break the cell membranes as the total area under the curve is smaller for both AASTY-A(+) and AASTY-A(−). Another possibility is that AASTY-A is unsuitable for the tested membrane protein. In contrast, AASTY-B and -C were affected to a much lesser extent by the end-group, and were about equally effective in the FSEC experiments. Notably, both variations of the AASTY-B and -C polymers were nearly as effective as SMA2000 in extracting $hTRPM_4$, though they consistently produced smaller discs than SMA2000, which were even smaller without the dodecyltrithiocarbonate end-group (FIG. 1D, panel B). Together, these results suggest that there is no benefit to a gradient in monomer distribution for AASTY.

Example 2: Refined AATSY Polymer Study

Based on the results with polymers A, B and C, it was decided to make a narrow library in terms of composition, varying the initial AA monomer fraction from 40-55% to further examine compositions close to those of B and C. It was also decided to remove the dodecytrithiocarbonate end-group and to increase the molecular weight range from 3-4 Da to 6-8 kDa. We synthesized four polymers, AASTY-D, -E, -F and -G, with initial [AA]:[STY] compositions of 60:40, 55:45, 50:50 and 45:55, respectively. See, e.g., FIG. 1A, polymers D to G.

Figure 2A:
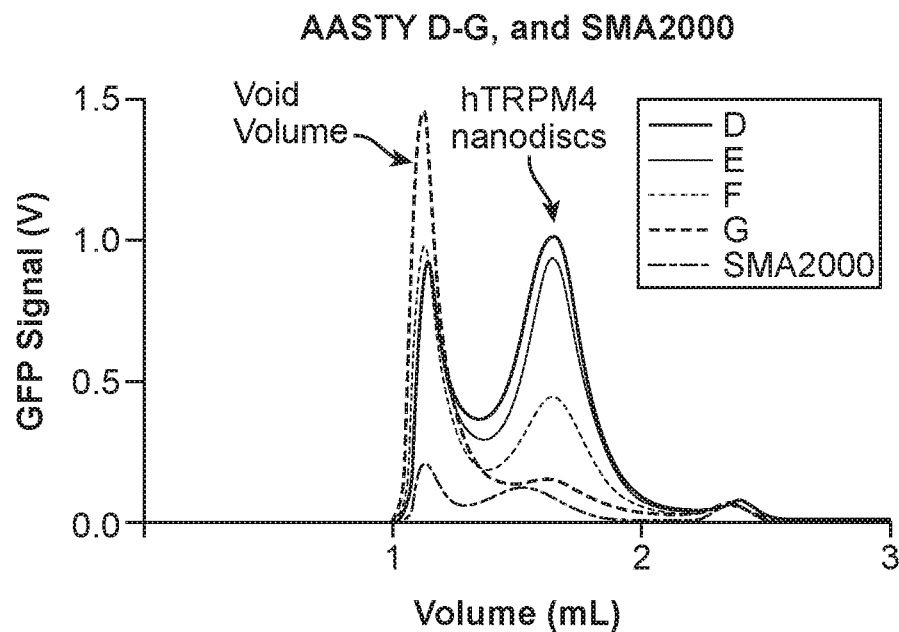
FIG. 2, panel A shows FSEC of hTRPM$_4$ extracted with AASTY polymers D, E, F, and G and the conventional SMA2000 polymer.
Figure 2B:
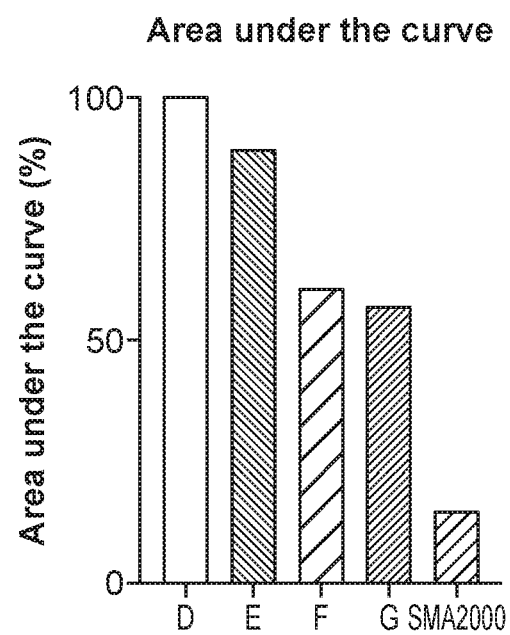

The FSEC traces with $hTRPM_4$ with AASTY-D, -E, -F, and -G shows that all four polymers can reconstitute $hTRPM_4$ and that D, E and F are more efficient at it than SMA2000 (FIG. 2, panel A). Particularly D and E are significantly more efficient than SMA2000. G is also efficient in solubilizing protein, however, the fraction of well-behaved reconstituted protein is comparable to SMA2000 (FIG. 2, panel A)

Purification of AASTY-E Reconstituted $hTRPM_4$

Based on the promising FSEC traces presented above, we purified $hTRPM_4$ in AASTY-E. Following an extraction protocol of $hTRPM_4$ similar to that with detergent described in Autzen et al. Protein Sci. (2018), 27, 155, was unsuccessful in retaining any protein on the affinity resin. Meanwhile, addition of 250 mM L-Arginine in the affinity binding- and elution buffer helped retain hTRPM$_4$ for further purification (FIG. 3, panel B)

Figure 3A:
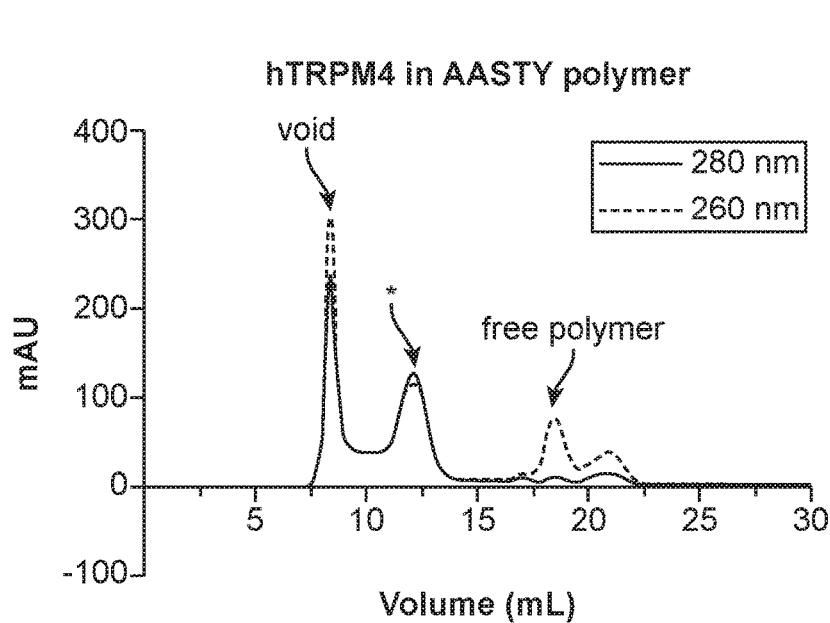
FIG. 3, panel A illustrates SEC traces from purification of hTRPM$_4$ in polymer E.
Figure 3B:
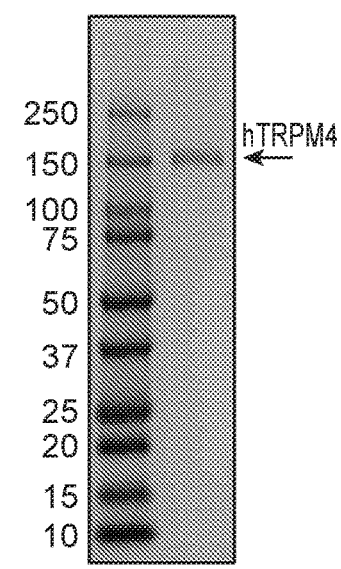
Figure 3C:
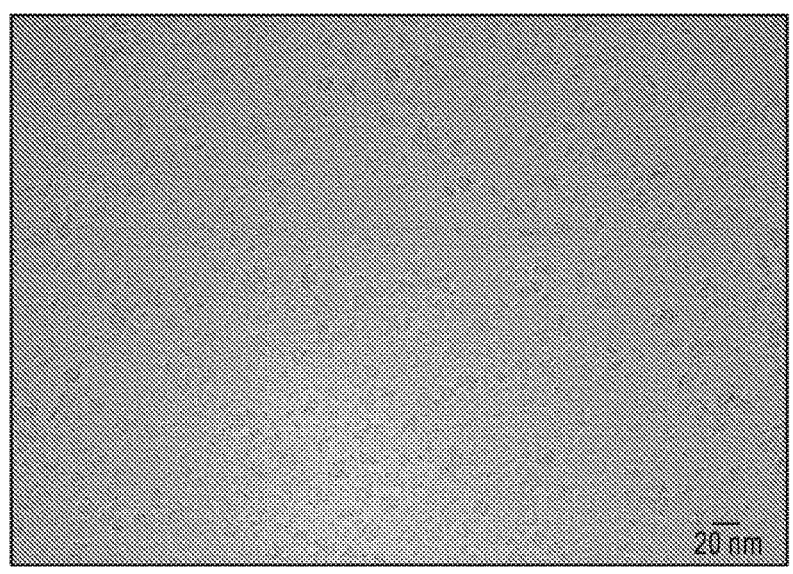
Figure 3D:
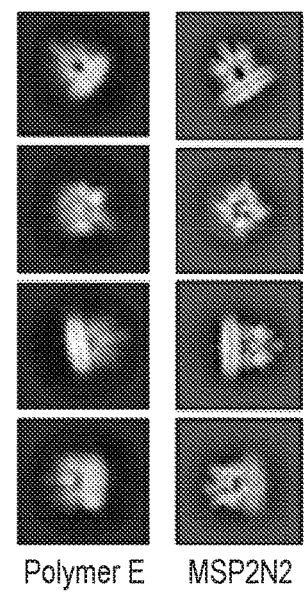

Injection of hTRPM$_4$ in AASTY-E onto a Superose 6 Increase SEC column produces a high void peak, but a decent nanodisc peak according to the absorption at 280 nm (FIG. 3A, lower trace).

Unfortunately, hTRPM$_4$ in AASTY-E is highly aggregated when analyzed with negative stain EM, which could be due to instability of the polymer towards the highly acidic uranyl formate stain, free $Cu^{2+}$ ions on the grid or protein instability in the nanodisc. Cryogenic preparation of hTRPM$_4$ in AASTY-E looked more promising than negative stain; however, the sample is still highly heterogeneous despite its high purity with few good particles in a single micrograph (FIG. 3, panel C). The 2D class averages of these particles show similarity to hTRPM$_4$ to identify the protein (FIG. 3, panel D), but were of insufficient quality to yield a structure of the protein. We suspect that this is due to protein aggregation at the air-water interface, as sample on grids with layers of graphene oxide (GO) functionalized with amine looks more homogenous. However, particles on these grids did not produce good 2D class averages. Altogether, despite the higher extraction efficacy of hTRPM$_4$, according to SEC and SDS page, AASTY required high ionic strength to facilitate binding of membrane proteins to affinity resins. Protein stability to these binding conditions is therefore pivotal for single particle cryo-EM of mammalian proteins using native nanodiscs.

Figure 4A:
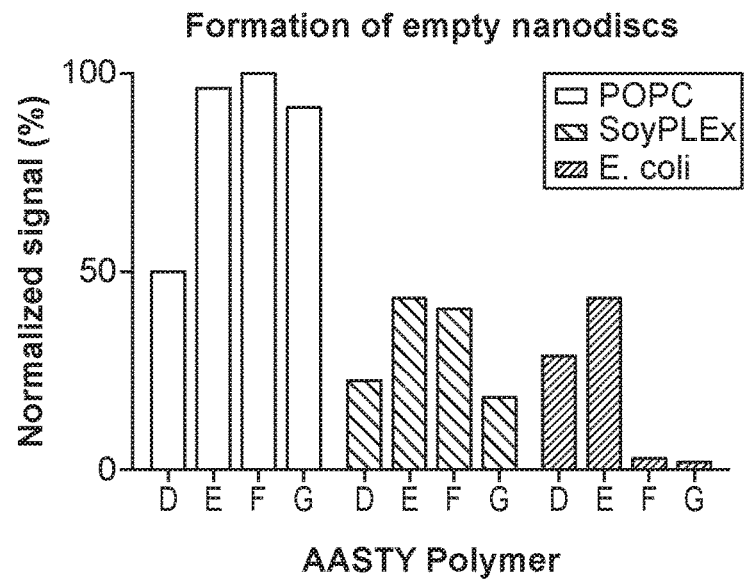
FIG. 4, panel A shows maximum fluorescence signals from FSEC with AASTY polymers D, E, F and G solubilizing either POPC, Soy polar lipid extract (Soy PLEx) and E. coli polar lipid extract (E. coli PLEx). Values are normalized relative to the highest detected signal.
Figure 4B:
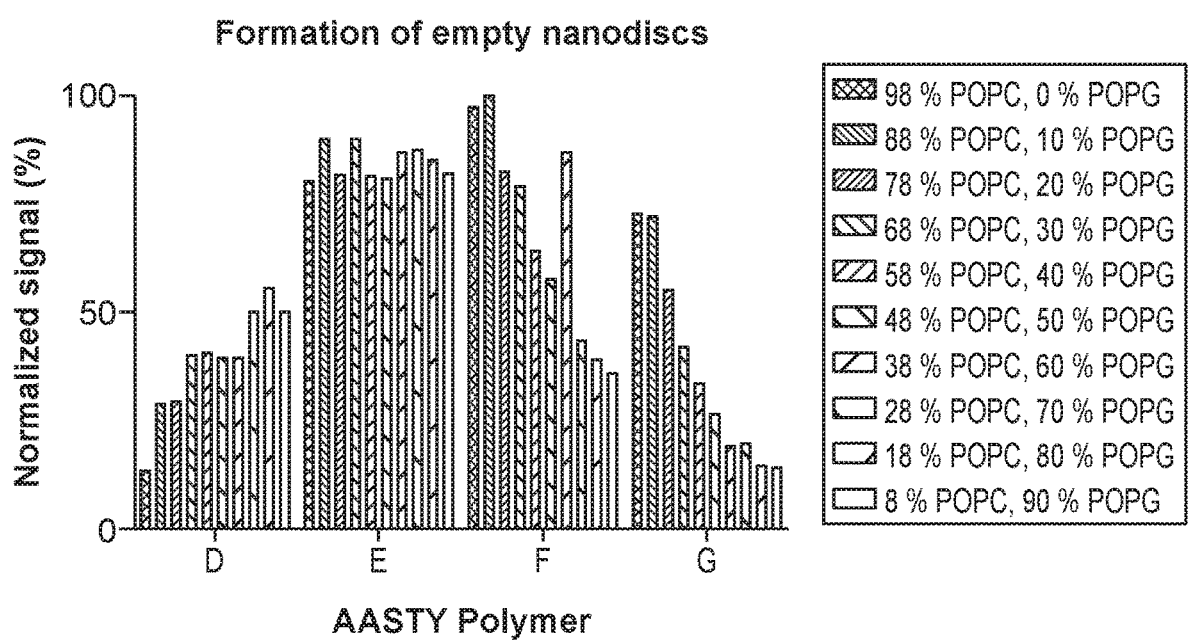
Figure 5:
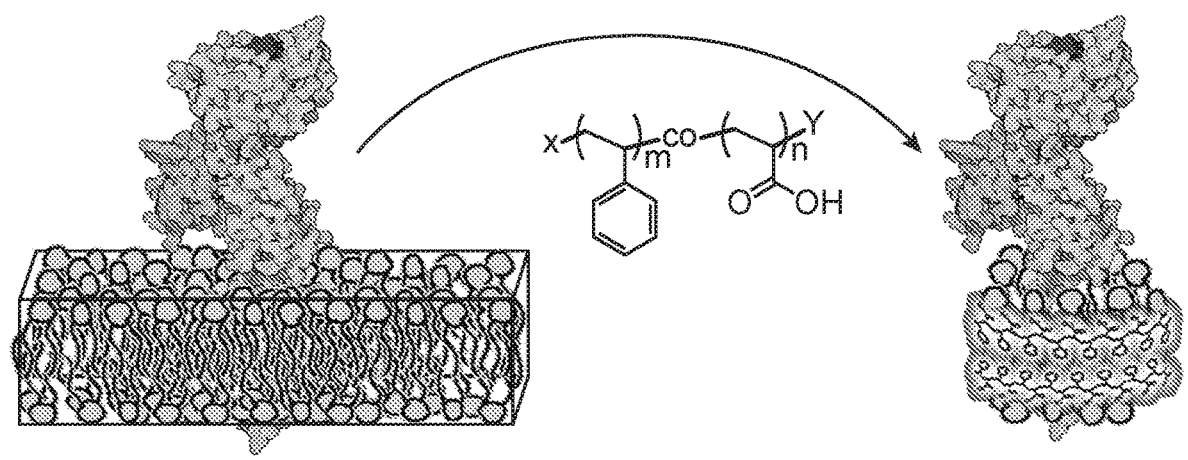
FIG. 5 depicts an exemplary acrylic acid-co-styrene lipid nanodisc assembly.
Figure 6:
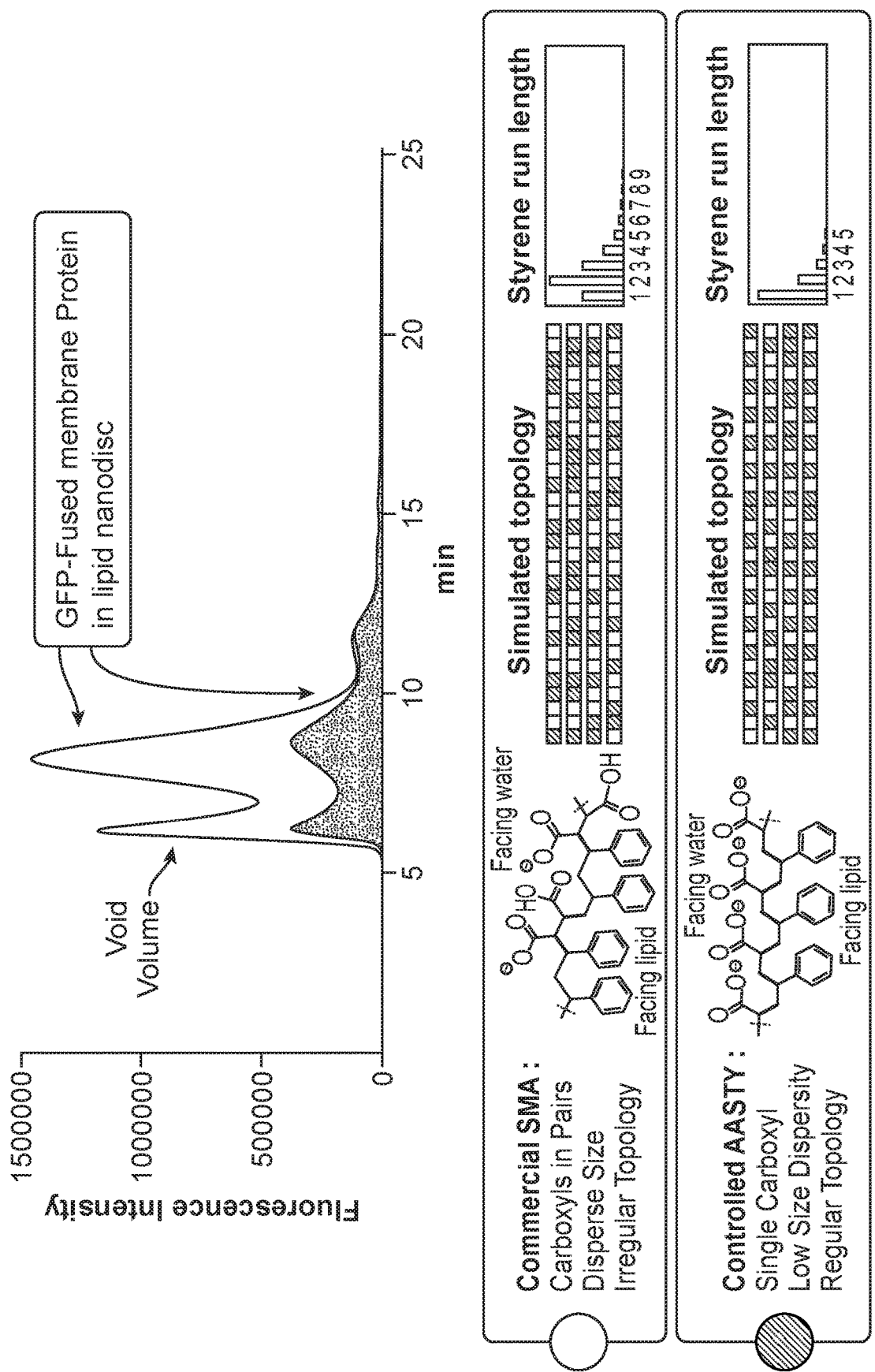
FIG. 6 depicts FSEC of exemplary AASTY copolymer lysed mammalian cells and commercial SMA lysed mammalian cells.
Figure 7A:
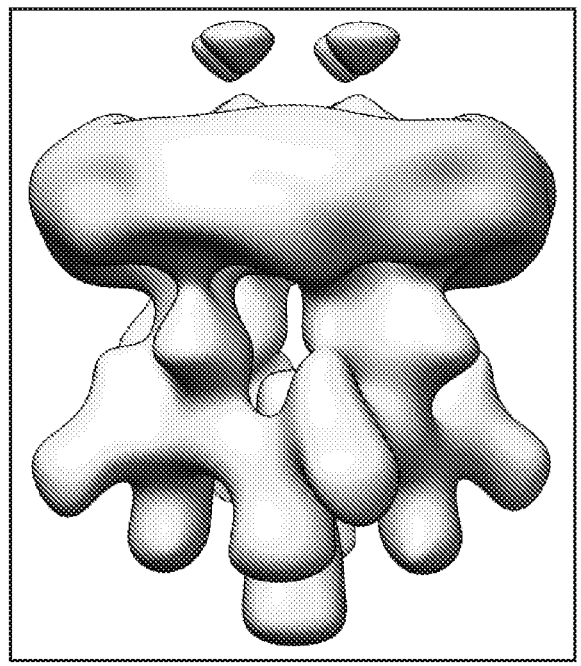
FIG. 7A-7B illustrates transmission electron cryomicroscopy (Cryo-EM) of hTRPM4 solubilized with AASTY Polymer E in exemplary AASTY nanodiscs.
Figure 7B:
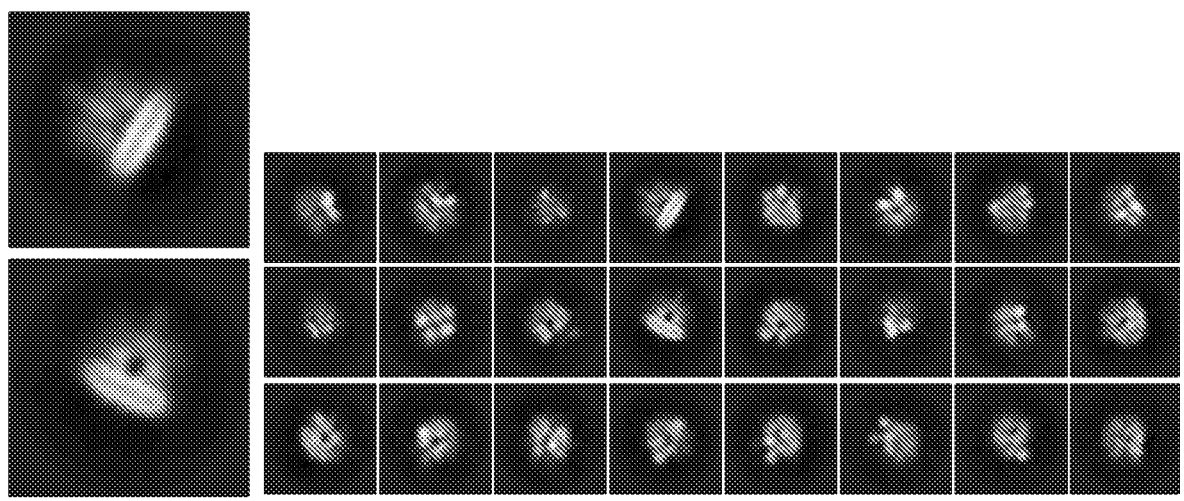
Figure 8:
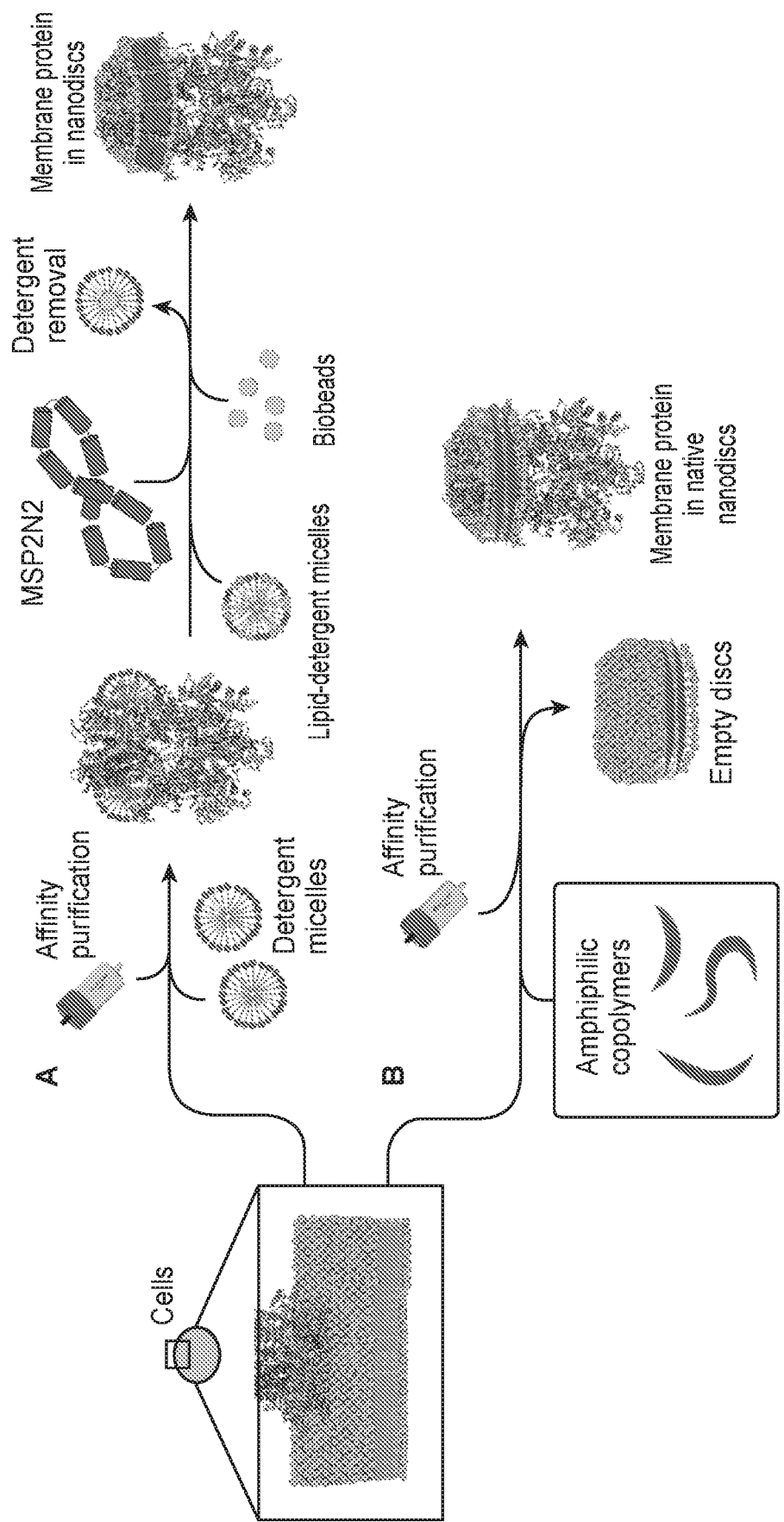
FIG. 8, panel A depicts purification of membrane proteins and reconstitution in lipid bilayers in belt forming proteins, such as MSP$_2$N$_2$. First cells are treated with detergent, followed by purification of the recombinant protein in detergent micelles by affinity chromatography. The purified protein is then reconstituted into a lipid bilayer with Belt forming proteins, and detergent is removed with biobeads.
Figure 8:
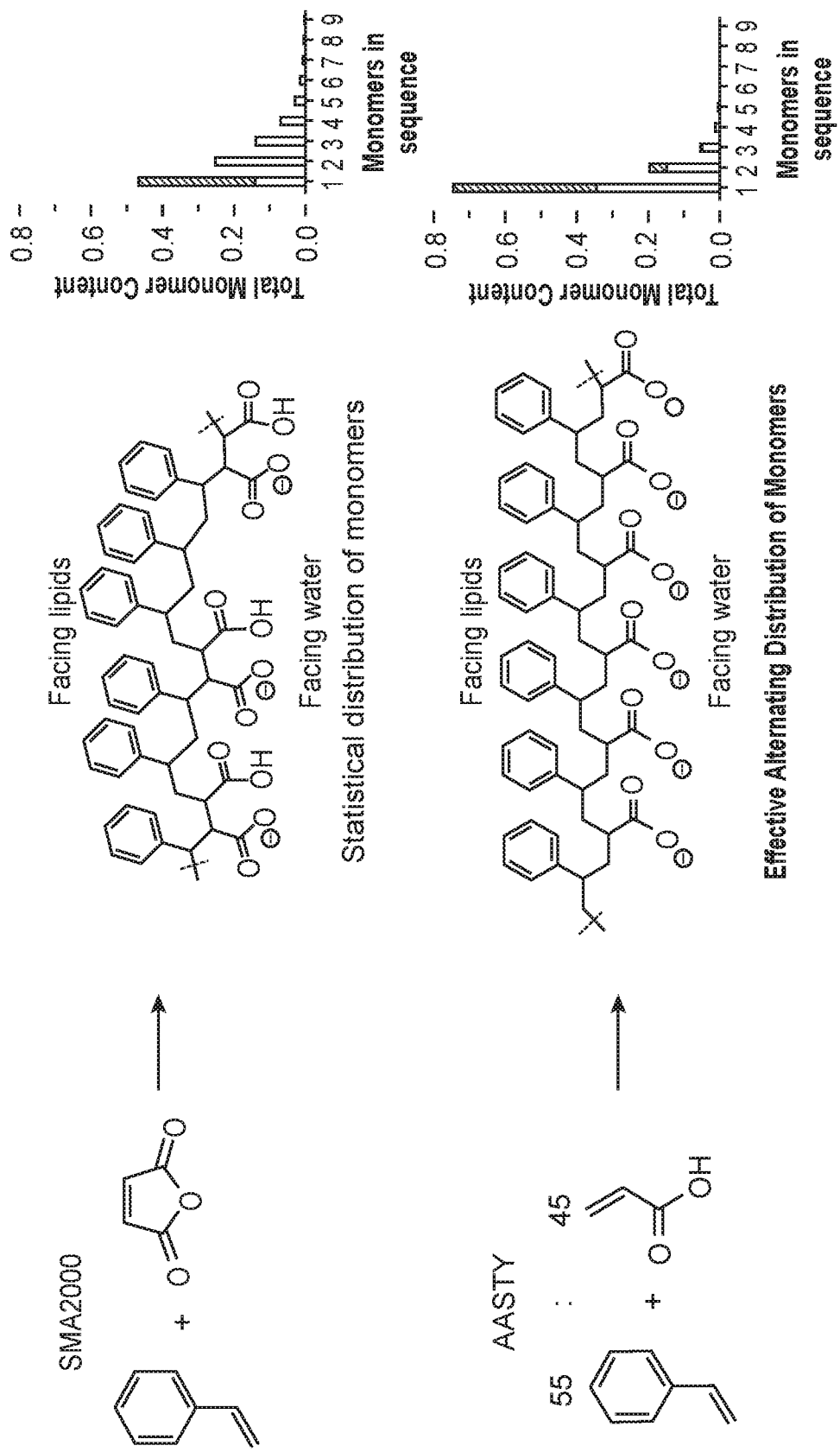

Example 3: Effect of Lipid Composition on the Solubilization Efficiency with AASTY In order to determine whether the lipid composition has an effect on the solubilization efficiency with AASTY, empty discs incorporating 2% of the fluorescent LisRhod PE lipid with three different lipid mixtures, POPC, SoyPLEx and E were made. coli PLEx. As seen from FIG. 4, panel A, the synthetic, zwitterionic lipid POPC forms nanodiscs with all four of polymers D, E, F and G. SoyPLEx also forms nanodiscs with all four AASTY polymers D, E, F and G, however, is much less soluble with the four AASTY polymers than POPC. E. coli lipids were able to form nanodiscs with the D and E polymers, but not the F and G polymers. We speculated whether this difference in solubility between POPC, SoyPLEx and E. coli lipids originated from the differences in charged lipid species; A major lipid component in E. coli PLEx is the negatively charged phosphatidylglycerol (PG) backbone. To shed light on the influence of the charge on the efficiency of the nanodisc formation, the synthetic variant of PG, POPG, was systematically varied together with POPC in ten different ratios with a constant 2 LisRhodPE and allowed to form nanodiscs with the AASTY polymers. AASTY-E is equally capable of solubilizing all the tested POPC:POPG ratios (FIG. 4, panel B). Meanwhile, nanodisc formation with AASTY-D is more efficient when increasing the amount of the negatively charged POPG, while the nanodisc formation is less efficient for AASTY-F and -G polymers with an increase in negative charge (FIG. 4, panel B). These differences in solubilization are pronounced, considering the modest differences in composition between the polymers. The data suggests that polymer E is generally most effective composition across the lipids tested. Moreover, the effectiveness of polymer E is supported by it also being the most effective at solubilizing hTRPM$_4$ (FIG. 2, panel A). We hypothesize that the effectivity of Polymer E is due to it having a functional sweet spot in the ratio of styrene to carboxylate pendant groups, being highly alternating in structure, while not exhibiting a gradient in composition along the chain, while also having a molecular weight in the optimum range. That E has an optimum ratio of carboxylate to styrene ratio is supported by the solubilization profiles of D and F (FIG. 4, panel B), which according to simulation should have less and more AA respectively. The lipid compositions they most effectively solubilize are mirrored in terms of charge, where D is most effective at solubilizing anionic lipid compositions, and F is most effective at solubilizing a more zwitterionic lipid compositions.

To further understand the influence of polymer sequence we applied the zero-order Markov model to the simulation output of 'Compositional Drift', the chemical correlation parameter lambda could be calculated, yielding a numerical measure of monomer sequence composition (Fredrickson et al. Macromolecules 1992, 25, 6341-6354). For reference, a $\lambda=0$ is a perfectly random copolymer $\lambda=$, $-1$ is a perfectly alternating copolymer while $\lambda=1$ is a di-block copolymer with equal DP in blocks. With reference to FIGS. 1A and IC, polymers E,F and G all have a $\lambda$ below $-0.7$ and more than 70% of all monomers are of run length 1, i.e., these copolymers are more than 70% alternating (FIG. 1A and FIG. 1C). Polymer F was the most alternating copolymer with a $\lambda=-0.76$, and it should be expected to be the most effective copolymer if regularity was the most dominating factor. This is not the case, which suggests that the ratio of carboxylate to styrene are more crucial for lipid solubilization. Interestingly, the polymer that is most effective, polymer E, is the one with the least amount of gradient formation i.e. the one polymerized closest to the azeotropic monomer composition, where the polymer composition is identical to the monomer composition, regardless of conversion. While less alternating than F, it is without a gradient and thus has the most homogeneous monomer composition along the chain.

Conveniently, these polymers form at monomer compositions close to the azeotropic point, meaning that these polymerizations can be taken to high conversions with limited or no gradient forming. This makes these polymers very straightforward to synthesize, as they do not need to be stopped at a specific conversion to attain the desired monomer distribution.

Example 4: Synthesis of Polymers

An exemplary synthetic procedure for producing a subject AASTY copolymer is shown in Scheme 1:

Scheme 1: General synthetic procedure for exemplary AASTY copolymers

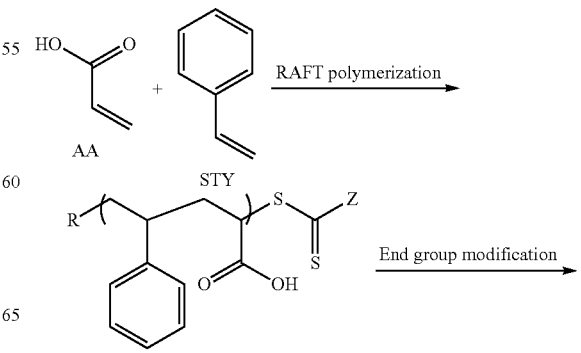

-continued

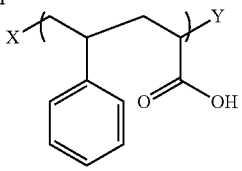

Copolymererizations were performed neat, with azobisisobuntyrunitrile (AIBN) as initiator, using 42-(Dodecylthiocarbonothioylthio)-2-methylpropionic acid (DDMAT) as the RAFT agent, resulting in a dodecyltrithiocarbonate endgroup. The ratios of styrene and acrylic acid were varied as denoted in Table 1. The polymers were performed neat, at [M]/[RAFT] of either 50 (A, B, C) or 100 (D, E, F, G). The polymers A, B, and C were performed by combining AA, STY, DDMAT, and AIBN in a Sclenck tubes. The reaction mixtures were degassed by four freeze-pump-thaw cycles, and then heated to 60° C. D, E, F, and G were made by parallel automated synthesis as described below (e.g., see Table 1). Due to the solvent free conditions and generally high conversions, the products had high viscosities or were solids. The crude reaction mixtures were diluted or dissolved in acetone, and the polymers were precipitated into diethylether, and the precipitate collected by filtration and dried in vacuo.

TABLE 1 synthesis of polymers

| | AA | | | STY | | | RAFT | | AIBN | |
|---|---|---|---|---|---|---|---|---|---|---|
| | mL | g | mmol | mL | g | mmol | g | mmol | g | mmol |
| A | 0.34 | 0.36 | 5 | 1.72 | 1.56 | 15 | 0.15 | 0.4 | 0.013 | 0.08 |
| B | 0.48 | 0.5 | 7 | 1.49 | 1.36 | 13 | 0.15 | 0.4 | 0.013 | 0.08 |
| C | 0.62 | 0.65 | 9 | 1.26 | 1.15 | 11 | 0.15 | 0.4 | 0.013 | 0.08 |
| D | 11 | 11.5 | 160 | 27.5 | 25 | 240 | 1.46 | 4.01 | 0.13 | 0.8 |
| E | 12.3 | 13 | 180 | 25.2 | 22.9 | 220 | 1.46 | 4.01 | 0.13 | 0.8 |
| F | 13.7 | 14.4 | 200 | 22.9 | 20.8 | 200 | 1.46 | 4.01 | 0.13 | 0.8 |
| G | 15.1 | 15.6 | 220 | 20.6 | 18.8 | 180 | 1.46 | 4.01 | 0.13 | 0.8 |

Large scale parallel syntheses of polymers D, E, F, and G were conducted on a Chemspeed SLTII automated synthesizer. The reactions were performed in 100 mL disposable ISynth reactors fitted with actively cooled reflux-condenser lids, and mixing was accomplished by vortex agitation. Temperature control was maintained by use of a Huber cryostat with an operational range of −20-150° C. All aspirations and dispensing of reagent solutions, were performed using a 4-Needle Head tool equipped with 2×1 mL and 2×10 mL syringes, with only the 10 mL syringes used in this particular experiment. All solvent lines were primed with 60 mL (6 strokes of syringe volume) of degassed dimethyl formaldehyde. Typical aspiration and dispense rates of the reagents were 5 mL/min and 10 mL/min, respectively for the 10 mL syringes. An airgap of 50 μL and an extra volume of 50 μL were used for all aspirations using the 4-Needle Head tool, and needles were rinsed after each reagent dispense task with a 30 mL inside and 30 mL outside volume of the priming solvent. The dimethyl formaldehyde reservoir was degassed by continuous nitrogen sparging. All stock solutions, freshly distilled styrene, acrylic acid, and a combined solution of DDMAT (250 mg/mL), and AIBN (23 mg/mL) in styrene were prepared in 60 mL septa-capped reagent vials, and were degassed by sparging with argon for 15 min and before being put in the Chemspeed. The atmosphere within the Chemspeed was reduced to <1% oxygen within 1 hour by purging with nitrogen while exhaust ports were closed. Reactors were set to open under nitrogen flow until the start of the reaction. The desired aliquots of stock solutions and solvent from the reservoir were transferred to the reactors with the automated liquid handling system before the reactors were set to closed-independent and were heated to 60° C. and vortex mixing of 400 rpm. Temperature control and mixing were continued for the full 5 hour duration of the reaction, at which time the temperature was rapidly dropped to 20° C.

For D, E, F, and G the dodecyltrithiocarbonate end groups were removed with $H_2O_2$ according to a modified procedure by Jesson et. al. *Abstr Pap Am Chem S* 254 (2017). Polymer (5 g) was dissolved in 40 mL of a 1:3 mixture of water:ethanol, 1.8 mL 30% $H_2O_2$, and the mixture was incubated at 70° C. overnight. The resulting colorless opaque solution was split into two 50 mL centrifuge tubes, and the polymer was precipitated by addition of water. Next, the precipitated polymer was spun down, the supernatant was discarded, and the isolated polymer was subsequently dried. Finally, the solid was washed with a 1:1 mixture of hexane:diethyl ether, and dried.

The polymers were converted into their sodium salts by dropwise addition of a saturated $NaHCO_3$ solution to a solution of polymer in a 1:1 EtOH:water mixture until pH was 7.6, and any residual particulates were removed by filtration through a 0.22 μm nylon syringe filter, and freezedried to recover the sodium salt of the polymer.

For polymers A B and C, the trithiocarbonate end-groups were removed from the polymers using hydrazine, followed by an in situ Michael addition of the resulting thiols to acrylamide. 20 eq of hydrazine, with respect to end groups, was added to 50 mg/mL aqueous solutions of the polymer salts. The reactions incubated at room temperature for 6 hours. This was followed by the addition of 200 eq acrylamide and incubated overnight. The polymers were recovered by precipitation with HCl(aq), and spun down in 50 mL centrifuge tubes and the supernatant discarded. The resulting precipitate was voluminous and retarded a significant amount of the solvent. It was dissolved in a small volume 1:1 water ethanol mixture, and re-precipitated by the addition of water to the tube. This precipitation was repeated a total of three times. Finally, the polymers were converted back to their sodium salt and freeze-dried. Due to the significantly larger scale of polymers D, E, F, and G this procedure was abandoned in favor of the $H_2O_2$ method described above.

Polymer characterization. Number-average (Mn) and weight-average (Mw) molar mass and dispersity (Đ=Mw/Mn) of polymers were obtained using size exclusion chromatography (SEC) carried out using a Dionex Ultimate 3000 instrument (including pump, autosampler, and column compartment) outfitted with a Dawn Heleos II Multi Angle Light Scattering detector, and a Optilab rEX refractive index detector. The column was a Superose 6 Increase 10/300 GL from GE healthcare. Data was analyzed using Astra 6.0 software. A do/dc of 0.170 mL/g was used for all samples. A Varian Inova 300 MHz NMR instrument was used to acquire $^1$H-NMR.

Analysis of Compositional Drift. The polymers were simulated using the 'Compositional Drift' analysis tool (Smith et al. *Acs Macro Letters*, 2019, 8, 36-40). This allows a visualization of the distribution of monomer run-lengths, while also calculating the $\lambda$-factor, allowing a numerical readout for alternating behavior and a comparison of polymer structure.

Example 5: Preparation of rTRPV$_5$ and hTRPM4 in AASTY Nanodiscs

Human transient receptor potential melastatin type 4 (hTRPM$_4$) fused with an N-terminal StrepTagII-eGFP tag and rTRPV5 with an N-terminal MBP tag were expressed in HEK$_{293}$F cells as described elsewhere (Abarca et al. *Inorg. Chem.* 2000, 39, 642-651). In short, 5 g of HEK2$_{93}$F cells either overexpressing rTRPV$_5$ or hTRPM$_4$ were resuspended in 10 mL Tris-buffered saline (TBS) [50 mM Tris-HCl, pH 8.0 at 4° C., 150 mM NaCl] supplemented with an EDTA-Free SIGMAFAST Protease Inhibitor Cocktail Tablet (Sigma) (Buffer A) and snap-frozen in liquid N$_2$ and stored at −80° C. until purification. hTRPM$_4$ was extracted from HEK$_{293}$F cells and analyzed either as crude lysate in FSEC for initial polymer screening or purified with affinity chromatography and SEC. rTRPV5 was purified with affinity chromatography and SEC.

Fluorescent Size Exclusion Chomatography. FSEC analysis of hTRPM$_4$ was carried out starting with either intact cells or isolated membranes. Starting from cells, 25 mg HEK$_{293}$F cells were resuspended in 200 uL TBS supplemented with EDTA-Free SIGMAFAST Protease Inhibitor Cocktail Tablets (Sigma). 50 uL of the cell suspension was mixed with 50 uL 2 or 4% (w/v) polymer solubilized in Tris-buffered saline (TBS) [50 mM Tris-HCl, pH 8.0 at 4° C., 150 mM NaCl] for a final concentration of 1 or 2% (w/v) and incubated on a rolling table for 2 hours at 4° C. Large aggregates were removed from the suspension by ultracentrifugation at 90.000 xg for 10 min and the supernatant was filtered with a 0.22 um spin filter unit before 1-10 uL sample was loaded onto a Superose6Increase column (5/150 GL) pre-equilibrated with TBS buffer. Separation was performed at a flow rate of 0.2 mL/min and the eluent was detected by a Shimadzu fluorometer with excitation wavelength of 488 nm, emission of 509 nm for detection of eGFP and a recording time of 20 min.

Protein Purification

Small-Scale Purification: For purification of hTRPM4, 600 μL of 80 mg/mL of HEK$_{293}$ membrane resuspended in TBS were mixed with neutralized AASTY polymer solution at a final concentration of 2% (w/v) and incubated on a rolling table for 2 hours at 4° C. After solubilization, the solution was ultracentrifugated at 90 000 xg for 10 minutes to pellet insoluble material. The soluble material was isolated, mixed with 250 mM L-Arginine, pH 7.4 and transferred to 200 μL TBS equilibrated StrepTactin Sepharose beads in batch. The nanodisc sample was incubated with the beads on a rolling table for 3 hours at 4° C. after which the unbound sample was collected (~600 μL) and the beads washed three times with 600 μTBS supplemented with 250 mM L-Arginine (TBS-A). The nanodisc sample was eluted from the beads with 200 μL TBS-A supplemented with 5 mM D-desthiobiotin for 2 hours at 4° C. The eluted nanodisc sample was collected using a 0.22 μm spin filter and injected onto a Superose6Increase 5/150 GL column (GE Life Sciences) equilibrated with TBS. Peak fractions were pooled and analyzed by SDS-PAGE, negative-stain EM and cryo-EM.

Large-Scale Purification: For large-scale purification of rTRPV$_5$ and hTRPM$_4$ in ASSTY nanodiscs, 5 g of cells were thawed and incubated with Buffer B (Buffer A supplemented with the ASSTY polymer) for two hours on a rolling table at 4° C. to extract the protein. Large aggregates were removed from the suspension by a low-speed centrifugation at 26,000×g for 30 min. The supernatant was filtered with a 0.22 μm filter and transferred to 1 mL pre-equilibrated StrepTactin resin (GE Life Sciences) and incubated overnight to allow binding of the StrepTagII-tagged hTRPM$_4$ (14 hours). 2 M L-Arg-HCl, pH 8.0 was added to a final concentration of 250 mM. Unbound material was washed off with 30 column volumes (CV) Buffer C (Buffer A supplemented with 250 mM L-Arg) and the StrepTagII-tagged protein was eluted with 2 CV Buffer D (Buffer C with 5 mM d-Desthiobiotin). The eluted protein was concentrated to ~2 mg/mL as assessed by a NanoDrop UV-Vis spectrophotometer (280 nm, 1 mg=1 Abs). Next, the sample was filtered with a 0.22 μm spin filter after which 400-500 μL was injected onto a Superose6Increase 10/300 GL column (GE Life Sciences) equilibrated with TBS. Peak fractions were pooled and concentrated. The purity and quality of the ASSTY reconstituted hTRPM4 was assessed by SDS-PAGE and cryo-EM.

Negative-Stain EM. Negative-stain EM grids of hTRPM$_4$ and rTRPV$_5$ in AASTY nanodiscs were prepared by applying 3 μL of sample at 0.125 mg/mL (280 nm, 1 Abs=1 mg/mL) to a glow-discharged Formvar/Carbon 400 mesh copper grid and stained with two rounds of 3 uL 3% (w/v) uranyl formate. Negative-stain EM grids were imaged on a Tecnai T20 microscope (FEI Company) operated at 200 kV and equipped with a TVIPS TemCam F816 (8K×8K) scintillator based CMOS camera (NIPS, Germany). Images were recorded at a nominal magnification of 62,000× and a defocus range of 1.5-3 μm underfocus.

Cryo-EM. Grids of rTRPV$_5$ and hTRPM$_4$ in ASSTY nanodiscs were prepared by applying 3 uL of the sample (2 mg/mL, nanodrop 280 nm, 1 Abs=1 mg/mL) to a glow-discharged Quantif oil R1.2/1.3 300-mesh copper holey carbon grid (Quantif oil, Micro Tools). The grids were plunge-frozen in liquid ethane using a Vitrobot Mark IV (FEI) with a blotting time of 7 seconds, at 10° C. and at 100% humidity. Datasets were collected on a FEI Talos Arctica (Thermo Fisher Scientific, US) operated at 200 kV and equipped with an X-FEG electron source. Images were recorded in super-resolution mode at a nominal magnification of 36,000× corresponding to a physical pixel size of 1.14 Å at the specimen level and a K3 Summit direct electron detector (Gatan, US). The defocus range was set to 0.5-2.0 μm underfocus. A total exposure of 3.2 seconds was used with a 0.04 second frame rate (80 total frames).

Summary

Provided herein are nanodisc forming polymers composed by acrylic acid (AA) and styrene (STY), referred to often herein as "AASTY". The AASTY polymers are synthesized through RAFT, which allows tight control of the molecular weight and the monomer gradient within the polymer. Seven different AASTY polymers were designed, composed by different ratios of AA to STY, whilst keeping the molecular weight comparable and testing the effect of the presence of the dodecyl terminal group from the RAFT reaction. It is shown that changing the chemical composition from maleic acid (MA) to AA forming the AASTY polymer, drastically increases the fraction of functional membrane-solubilizing polymer compared to the SMA2000 polymer conventionally used. By adding the AASTY polymer to synthetic lipids as well as mammalian cells with recombinantly overexpressed integral membrane proteins, it is shown that this new polymer is a highly efficient and promising alternative to known polymers.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A composition comprising:
   a lipid; and
   a copolymer, wherein the copolymer comprises monomer units of styrene, and monomer units selected from acrylic acid, and an acrylic acid derivative;
   wherein the lipid and copolymer are in the form of a nanodisc assembly.

2. The composition of claim 1, wherein the acrylic acid derivative is selected from acrylate, acrylate ester, acrylamide, and N-substituted acrylamide.

3. The composition of claim 1, wherein the copolymer comprises an acrylic acid, or an acrylic acid derivative content of from 30 molar % to 70 molar % or from 35 molar % to 50 molar %.

4. The composition of claim 1, wherein the copolymer is a copolymer of styrene and acrylic acid, optionally with high regularity of alternating monomer units.

5. The composition of claim 1, wherein the copolymer is a diblock copolymer described by formula (I):

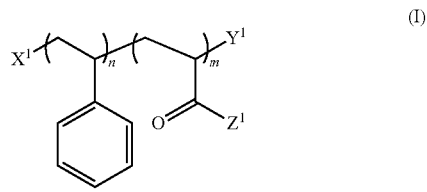

wherein:
$Z^1$ is selected from $OR^1$, and $NR^2_2$, wherein $R^1$ is selected from hydrogen, sodium, potassium, alkyl, and substituted alkyl, and each $R^2$ is independently selected from hydrogen, alkyl, and substituted alkyl;
$X^1$ and $Y^1$ are each independently a terminal group; and
n and m are each independently an integer from 15-100.

6. The composition of claim 5, wherein $Z^1$ is $OR^1$ and $R^1$ is hydrogen.

7. The composition of claim 5, wherein $Z^1$ is $OR^1$ and $R^1$ is alkyl or substituted alkyl.

8. The composition of claim 5, wherein $Z^1$ is $NR^2_2$ and each $R^2$ is selected from hydrogen, alkyl and substituted alkyl.

9. The composition of claim 8, wherein one $R^2$ is hydrogen and the other $R^2$ is alkyl or substituted alkyl.

10. The composition of claim 5, wherein $X^1$ is selected from alkyl, substituted alkyl, nitrile, hydroxy, carboxyl, and halogen.

11. The composition of claim 5, wherein $X^1$ is of the formula (X-I):

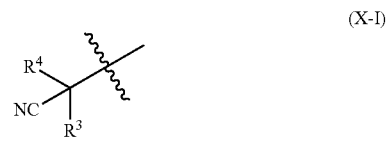

wherein:
$R^3$ and $R^4$ are each independently selected from hydrogen, alkyl, and substituted alkyl.

12. The composition of claim 5, wherein $Y^1$ is selected from, alkyl, substituted alkyl, nitrile, hydroxy, carboxyl, halogen, thiol, substituted thiol, acyl, and substituted acyl.

13. The composition of claim 5, wherein $Y^1$ is of the formula (Y-I)

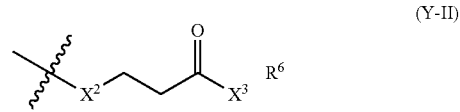

wherein:

$R^5$ and $R^6$ are each independently selected from hydrogen, alkyl, and substituted alkyl; and $X^2$ and $X^3$ are each independently selected from S and O.

14. The composition of claim 13, wherein the formula (Y-II) is of formula (Y-III):

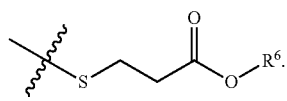

(Y-III)

15. The composition of claim 5, wherein n and m are each independently an integer from 15-50.

16. The composition of claim 1, wherein the molecular weight of the copolymer is from 2 kDa to 15 kDa or from 3 kDa to 8 kDa.

17. The composition of claim 1, wherein the nanodisc assembly has a diameter from 5 to 40 nm.

18. The composition of claim 5, wherein the copolymer is described by formula (II):

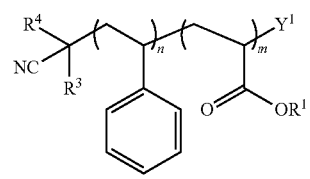

(II)

wherein:

$R^1$, $R^3$, and $R^4$ are each independently selected from hydrogen, alkyl, and substituted alkyl;

$Y^1$ is selected from:

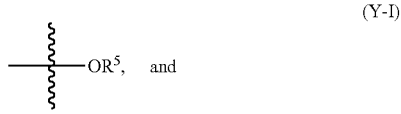

(Y-I)

and

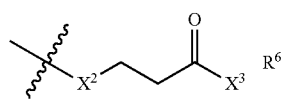

(Y-II)

wherein:

$R^5$ and $R^6$ are each independently selected from hydrogen, alkyl, and substituted alkyl;

$X^2$ and $X^3$ are each independently selected from S and O; and n and m are each independently an integer from 15-100.

19. The composition of claim 18, wherein the copolymer is described by the formula (III) or (IV):

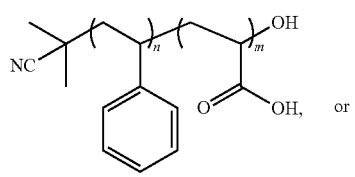

(III)

or

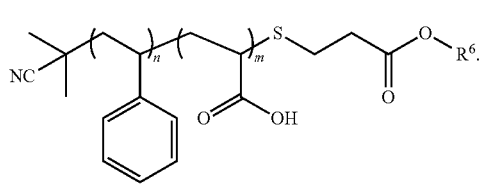

(IV)

20. The composition of claim 1, further comprising a membrane protein.

21. An aqueous solution comprising a composition according to claim 1.

* * * * *